(12) United States Patent
Merril

(10) Patent No.: US 6,740,492 B2
(45) Date of Patent: May 25, 2004

(54) HIGH SENSITIVITY PHAGE DISPLAY BIOMOLECULE DETECTION

(75) Inventor: Carl Merril, Bethesda, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 111 days.

(21) Appl. No.: 09/976,667

(22) Filed: Oct. 10, 2001

(65) Prior Publication Data

US 2002/0110806 A1 Aug. 15, 2002

Related U.S. Application Data

(63) Continuation of application No. PCT/US00/10146, filed on Apr. 13, 2000.
(60) Provisional application No. 60/129,215, filed on Apr. 14, 1999.

(51) Int. Cl.[7] .......................... C12Q 1/68; G01N 33/53
(52) U.S. Cl. ........................................... 435/6; 435/7.1
(58) Field of Search ................... 435/6, 7.1; 536/23.1, 536/24.3; 530/350

(56) References Cited

U.S. PATENT DOCUMENTS

| | | | |
|---|---|---|---|
| 5,223,409 A | | 6/1993 | Ladner et al. |
| 5,458,760 A | * | 10/1995 | Kozulic |
| 5,650,267 A | * | 7/1997 | Ray et al. |
| 5,679,510 A | * | 10/1997 | Ray et al. |
| 5,702,892 A | | 12/1997 | Mulligan-Kehoe |
| 6,114,115 A | * | 9/2000 | Wagner, Jr. |

FOREIGN PATENT DOCUMENTS

| | | |
|---|---|---|
| EP | 0617737 | 1/1997 |
| EP | 0844306 | 5/1998 |
| WO | 97/00329 | 1/1997 |
| WO | 97/22972 | 6/1997 |
| WO | 98/15833 | 4/1998 |

OTHER PUBLICATIONS

Aujame, L, et al. (1997) High affinity human antibodies by phage display, Human Antibodies 8(4):155–168.
Barbas, C, F., et al. (1991) Assembly of combinational antibody libraries on phage surfaces: The gene III site. PNAS 88:7978–7982.
Bradbury, A. (1997) Meeting Report advances In phage display: the report of the Phage Club first meeting, Immunotechnology 3:227–231.
Chester, K.A., et al. (Mar. 27–30, 1994) A High Affinity Anti–CEA scFv for Tumour Targeting Produced in Fllamentous Phage. Br. J. Cancer 69(Suppl 21):15.
Hagag, N. G., et al. (1990) Molecular Cloning of Proteinase–Encoding Genes from Cancer Cells by Zymogen Assay and Direct Sequencing. Anal. Blochem. 191:235–241.
Merz, D. C., et al. (1995) Generating a phage display antibody library against an identified neuron. J. Neuroscience Methods 62:213–219.
Nissim, A., et al. (1994) Antibody fragments from a 'single pot' phage display library as immunochemical reagents, EMBO J. 13(3):692–698.
Persson, M. A., et al. (1991) Generation of diverse high–affinity human monoclonal antibodies by repertoire cloning. PNAS 88:2432–2436.
Watkins, J.D., et al. (1998) Discovery of Human Antibodies to Cell Surface Antigens by Capture Lift Screening of Phage–Expressed Antibody Libraies. Analytical Biochem. 256:169–177.

* cited by examiner

Primary Examiner—Ethan Whisenant
(74) Attorney, Agent, or Firm—Knobbe, Martens, Olson & Bear LLP

(57) ABSTRACT

The invention relates to a biomolecular complex comprising a target biomolecule; a phage having a phage-expressed binding protein that can bind to the target biomolecule or having joined thereto a linked or un-linked protein or nucleic acid that can bind to the target biomolecule, wherein the phage-expressed binding protein or the linked or unlinked protein or nucleic acid is bound to the target biomolecule to provide a bound phage; and a host bacterial cell that is a host for the phage under conditions that permit the bound phage to infect the host.

5 Claims, 8 Drawing Sheets

SEQUENCE LISTING

```
<160> NUMBER OF SEQ ID NOS: 15

<210> SEQ ID NO 1
<211> LENGTH: 48
<212> TYPE: DNA
<213> ORGANISM: Artificial Sequence
<220> FEATURE:
<223> OTHER INFORMATION: Cloning Oligonucleotide

<400> SEQUENCE: 1
ggatccgggg gtattaatat gacgggtacc agcaaagaaa cctttacc                48

<210> SEQ ID NO 2
<211> LENGTH: 32
<212> TYPE: DNA
<213> ORGANISM: Artificial Sequence
<220> FEATURE:
<223> OTHER INFORMATION: Cloning Oligonucleotide

<400> SEQUENCE: 2
atcggccggt cgacttaaac gatgctgatt gc                                 32

<210> SEQ ID NO 3
<211> LENGTH: 23
<212> TYPE: DNA
<213> ORGANISM: Artificial Sequence
<220> FEATURE:
<223> OTHER INFORMATION: Cloning Oligonucleotide

<400> SEQUENCE: 3
ccggggatcc tcaactgtga gga                                           23

<210> SEQ ID NO 4
<211> LENGTH: 37
<212> TYPE: DNA
<213> ORGANISM: Artificial Sequence
<220> FEATURE:
<223> OTHER INFORMATION: Cloning Oligonucleotide

<400> SEQUENCE: 4
atggccccgg gggccgtcat aaacatccct tacactg                            37

<210> SEQ ID NO 5
```

```
<211> LENGTH: 38
<212> TYPE: DNA
<213> ORGANISM: Artificial Sequence
<220> FEATURE:
<223> OTHER INFORMATION: Cloning Oligonucleotide

<400> SEQUENCE: 5 ttggccccg gggccagcaa agaaaccttt acccatta                              38

<210> SEQ ID NO 6
<211> LENGTH: 23
<212> TYPE: DNA
<213> ORGANISM: Artificial Sequence
<220> FEATURE:
<223> OTHER INFORMATION: Cloning Oligonucleotide

<400> SEQUENCE: 6
tgcccttaag cacggcagaa act                                             23

<210> SEQ ID NO 7
<211> LENGTH: 73
<212> TYPE: DNA
<213> ORGANISM: Artificial Sequence
<220> FEATURE:
<223> OTHER INFORMATION: Cloning Oligonucleotide

<400> SEQUENCE: 7
gaattcagcg ccgcatagc cgaccgggcc aaattctatc gaaggtcgtg ggactccgac      60
cccgaccact ccc                                                        73

<210> SEQ ID NO 8
<211> LENGTH: 33
<212> TYPE: DNA
<213> ORGANISM: Artificial Sequence
<220> FEATURE:
<223> OTHER INFORMATION: Cloning Oligonucleotide

<400> SEQUENCE: 8
aatggccccg ggggccgtaa tcatggtcat agc                                  33

<210> SEQ ID NO 9
<211> LENGTH: 44
<212> TYPE: DNA
<213> ORGANISM: Artificial Sequence
<220> FEATURE:
<223> OTHER INFORMATION: Cloning Oligonucleotide

<400> SEQUENCE: 9
aacggccgaa tgctagcgat aacgatgctg attgccgttc cggc                      44

<210> SEQ ID NO 10
<211> LENGTH: 29
<212> TYPE: DNA
<213> ORGANISM: Artificial Sequence
<220> FEATURE:
<223> OTHER INFORMATION: Cloning Oligonucleotide

<400> SEQUENCE: 10
aacggccgct ttacccttca tcactaaag                                       29

<210> SEQ ID NO 11
<211> LENGTH: 23
<212> TYPE: DNA
<213> ORGANISM: Artificial Sequence
<220> FEATURE:
<223> OTHER INFORMATION: Cloning Oligonucleotide
```

```
<400> SEQUENCE: 11
tgcccttaag cacggcagaa act                                                    23

<210> SEQ ID NO 12
<211> LENGTH: 29
<212> TYPE: DNA
<213> ORGANISM: Artificial Sequence
<220> FEATURE:
<223> OTHER INFORMATION: Cloning Oligonucleotide

<400> SEQUENCE: 12
aagctagcag ctggcctgtt gggcccact                                              29

<210> SEQ ID NO 13
<211> LENGTH: 41
<212> TYPE: DNA
<213> ORGANISM: Artificial Sequence
<220> FEATURE:
<223> OTHER INFORMATION: Cloning Oligonucleotide

<400> SEQUENCE: 13
aacggccgct atctatctag aattcgagct cggtacccgg g                                41

<210> SEQ ID NO 14
<211> LENGTH: 30
<212> TYPE: DNA
<213> ORGANISM: Artificial Sequence
<220> FEATURE:
<223> OTHER INFORMATION: Cloning Oligonucleotide

<400> SEQUENCE: 14
ttctgcagcg cgcaacacga tgaagctcaa                                             30

<210> SEQ ID NO 15
<211> LENGTH: 26
<212> TYPE: DNA
<213> ORGANISM: Artificial Sequence
<220> FEATURE:
<223> OTHER INFORMATION: Cloning Oligonucleotide

<400> SEQUENCE: 15
ttggtaccgc tcaccgaagg atcgtc                                                 26
```

HIGH SENSITIVITY PHAGE DISPLAY BIOMOLECULE DETECTION

CROSS-REFERENCE TO RELATED APPLICATIONS

This application is a continuation of international application number PCT/US00/10146 having international filing date of Apr. 13, 2000, designating the United States of America and published in English, which claims the benefit of priority of U.S. provisional patent application No. 60/129,215, filed Apr. 14, 1999; both of which are hereby expressly incorporated by reference in their entireties.

FIELD OF THE INVENTION

The invention described herein generally relates to the field of biomolecule detection. More specifically, the invention concerns novel compositions and methods for the detection of a biomolecule using cell or viral propagation as an indicator of the presence and location of the biomolecule.

BACKGROUND OF THE INVENTION

In order to understand the complexity of many biological systems, it necessary to use molecular detection techniques that enable a high degree of sensitivity and specificity. A number of organic stains have been adapted for the detection of electrophoretically separated proteins, for example, including Bromphenol Blue, Fast Green (Food Green 3) and Amido Black (Acid Black 1). (Durrem, *J. Am. Chem. Soc.* 72:2943 (1950) and Grassman and Hannig, *Z. Physiol. Chem.* 290:1 (1952)). Of the organic stains, Coomassie Blue has proved to be one of the most sensitive. (Fazekas De St. Groth et al., *Biochim. Biophys. Acta* 71:377 (1963) and Meyer and Lamberts, *Biochim. Biophys. Acta* 107:144 (1965)).

Fluorescent stains, such as fluorescamine are also used to detect proteins and have been shown to detect as little as 6 nanograms of myoglobin. (Ragland et al., *Anal. Biochem.* 59:24 (1974) and Pace et al., *Biochem. Biophys. Res. Commun.* 57:482 (1974)). A related compound, 2-methoxy-2,4-diphenyl-3(2H)-Furanone (MDPH), has the same speed and simplicity of reaction as fluorescamine and can detect as little as one nanogram of protein. Currently, the most sensitive technique for staining proteins is silver staining. In ideal conditions silver staining can detect as little as 0.01 nanogram of protein. (Merril et al., *Proc. Natl. Acad. Sci. USA* 76:4335 (1979) and Switzer et al., *Anal Biochem.* 98:231 (1979)).

Although organic stains, fluorescent stains, and silver staining are quite suitable for many molecular biological applications, the detection of a protein with a high degree of sensitivity is difficult. For example, 0.01 nanogram of a protein of molecular weight 30,000 Da represents 200,000,000 molecules of protein. Since the average number of molecules of a specific protein per cell is 5,000, the limit of current methods of protein detection is on the order of several thousand cells.

Similarly, the detection of nucleic acid sequences with a high degree of sensitivity is difficult. To perform in situ hybridization and Southern and Northern hybridization techniques, for example, several nanograms of target nucleic acid are needed and detection can require several weeks of exposure to autoradiography film. The capacity to amplify specific segments of nucleic acid, made possible by the Polymerase Chain Reaction (PCR), at least in theory, allows an investigator to detect a single molecule of nucleic acid. In practice, however, PCR with minute quantities of template is extremely difficult due to the proclivity of contamination of the sample reaction. (Erlich, ed., *PCR Technology, Principles and Applications for DNA Amplification*, Freeman & Co., publishers, New York, page 4 (1992)). In view of the foregoing, and notwithstanding the various efforts exemplified in the prior art, there remains a need for compositions and methods for highly sensitive biomolecule detection.

BRIEF SUMMARY OF THE INVENTION

Compositions and methods based on the discovery of a highly sensitive biomolecule detection system are disclosed. Generally, the biomolecule detection system described herein uses cell growth and/or viral propagation as a marker for the presence and location of a target biomolecule. That is, a cell or viral particle that displays a molecule that binds to the target biomolecule can be used to identify the presence and location of very small amounts of a target molecule disposed on a support by monitoring cell or viral propagation. Accordingly, many embodiments are practiced by providing a target biomolecule disposed on a support, contacting said target biomolecule with a cell or virus that displays a molecule that binds to said target biomolecule, removing any non-bound or non-specifically bound cells or virus, culturing the cells bound to the target biomolecule or infecting host cells with the virus-bound target, and determining the presence or location of the target biomolecule by detecting the presence of cell growth or plaques.

In one embodiment, for example, a method of detecting the presence of a biomolecule on a support is accomplished by providing a support having disposed thereon a biomolecule and contacting the biomolecule with a collection of phage, wherein individual phage in the collection have a phage-expressed binding protein so that the collection of phage in aggregate comprises a collection of phage-expressed binding proteins and wherein contact of the biomolecule and the collection of phage results in a non-bound population of phage and a bound population of phage. Subsequently, the non-bound population of phage is removed in a manner that retains the bound population of phage and the bound population of phage is placed together with a host for the phage under conditions that permit the bound phage to infect the host so as to produce a replicated population of phage. The presence of the biomolecule is then determined by detecting the replicated population of phage.

In several aspects of this embodiment, the biomolecule is selected from the group consisting of a lipid, a carbohydrate, a protein, and a nucleic acid and the biomolecule is separated by a one-dimensional or a two-dimensional procedure. Additionally, the support can be selected from the group consisting of a gel, a membrane, a filter, a paper, a chromatography matrix, and a chromatography resin and the gel can have a plastic backing. Preferably, a suspension of phage is contacted with the biomolecule and the unbound population of phage are removed by washing with a buffer. The phage suspension and washing buffer can contain blocking agents including but not limited to, casein, nonfat milk, bovine serum albumin, gelatin, tRNA, and a non-ionic detergent (e.g. Tween or NP-40) to reduce non-specific binding and facilitate removal of non-bound phage. Once the non-bound and non-specifically bound phage are removed, the bound population of phage is replicated on a lawn of host bacteria. The presence of the target protein is then detected by observing bacterial cell lysis. This aspect can also include a step whereby at least one phage from the replicated population of phage is isolated and the phage is incorporated into a pharmaceutical product, a biotechnological tool, or a diagnostic kit.

Another method of detecting the presence of a biomolecule on a support involves providing a support having a biomolecule disposed thereon and contacting the biomolecule with a collection of phage, wherein individual phage in the collection are joined to a protein that can bind to the biomolecule so that the collection of phage in aggregate comprises a collection of proteins that can bind to the biomolecule and, wherein contact of the biomolecule and the collection of phage results in a non-bound population of phage and a bound population of phage. After binding, as above, the non-bound population of phage is removed in a manner that retains the bound population of phage and the bound population of phage is placed together with a host for the phage under conditions that permit the bound phage to infect the host so as to produce a replicated population of phage. The replicated population of phage is then detected and, from this detection step, the presence of the biomolecule is determined.

In some aspects of this embodiment, the protein is joined to the phage by a linker including, but not limited to, avidin or strepavidin or a derivative thereof. Further, the biomolecule can be selected from the group consisting of a lipid, a crabohydrate, a protein, and a nucleic acid and the biomolecule can be separated by a one-dimensional or a two-dimensional procedure. The support can be selected from the group consisting of a gel, a membrane, a filter, a paper, a chromatography matrix, and a chromatography resin and the gel can have a plastic backing. Preferably, a suspension of phage is contacted with the biomolecule and the unbound population of phage are removed by washing with a buffer. The phage suspension and washing buffer can contain blocking agents including but not limited to, casein, nonfat milk, bovine serum albumin, gelatin, tRNA, and a non-ionic detergent (e.g. Tween or NP-40) to reduce non-specific binding and facilitate removal of non-bound phage. The bound population of phage is replicated on a lawn of host bacteria; and the protein is detected by observing bacterial cell lysis.

By another approach, the detection of a biomolecule on a support is accomplished by providing a support having disposed thereon a biomolecule and contacting the biomolecule with a collection of phage, wherein individual phage in the collection are joined to a nucleic acid that can bind to the biomolecule so that the collection of phage in aggregate comprises a collection of nucleic acids that can bind to the biomolecule, and wherein contact of the biomolecule and the collection of phage results in a non-bound population of phage and a bound population of phage. After binding, the non-bound population of phage is removed in a manner that retains the bound population of phage and the bound population of phage is placed together with a host for the phage under conditions that permit the bound phage to infect the host so as to produce a replicated population of phage. Next, the replicated population of phage are detected, which identifies the presence of the biomolecule.

In several aspects of this embodiment, the nucleic acid is biotinylated and is joined to the phage by a linker, wherein the linker comprises avidin or streptavidin or a derivative thereof. In many of these embodiments, the biomolecule is selected from the group consisting of a lipid, a carbohydrate, a protein, and a nucleic acid. The method can also involve separating the biomolecule by a one-dimensional or a two-dimensional procedure and the support can be selected from the group consisting of a gel, a membrane, a filter, a paper, a chromatography matrix, a chromatography resin, or a gel with a plastic backing. Preferably, a suspension of phage is contacted with the biomolecule and the unbound population of phage are removed by washing with a buffer. As with other embodiments, the phage suspension and washing buffer can contain blocking agents including but not limited to, casein, nonfat milk, bovine serum albumin, gelatin, tRNA, and a non-ionic detergent (e.g. Tween or NP-40) to reduce non-specific binding and facilitate removal of non-bound phage. The bound population of phage is replicated on a lawn of host bacteria and the presence and location of the protein is detected by observing bacterial cell lysis.

Methods of detecting the presence of a biotinylated biomolecule on a support are also included. By one approach, the method is accomplished by providing a support having disposed thereon a biotinylated biomolecule; contacting the biotinylated biomolecule with a collection of phage, wherein individual phage in the collection have a phage-expressed binding protein that binds to biotin, and wherein contact of the biotinylated biomolecule and the collection of phage results in a non-bound population of phage and a bound population of phage. After binding, the non-bound population of phage is removed in a manner that retains the bound population of phage and the bound population of phage is placed together with a host for the phage under conditions that permit the bound phage to infect the host so as to produce a replicated population of phage. By detecting the replicated population of phage, the presence and location of the biotinylated biomolecule is determined.

In several aspects of this embodiment, the phage-expressed binding protein comprises avidin or strepavidin or a derivative thereof and the biotinylated biomolecule is selected from the group consisting of a lipid, a carbohydrate, a protein, and a nucleic acid. The biotinylated biomolecule can be separated by a one-dimensional or a two-dimensional procedure and the support can be selected from the group consisting of a gel, a membrane, a filter, a paper, a chromatography matrix, and a chromatography resin. For some applications, a gel having a plastic backing is used. Preferably, a suspension of phage is contacted with the biomolecule and the non-bound population of phage are removed by washing with a buffer. Desirably, the phage suspension and washing buffer contain blocking agents including but not limited to, casein, nonfat milk, bovine serum albumin, gelatin, tRNA, and a non-ionic detergent (e.g. Tween or NP-40) to reduce non-specific binding and facilitate removal of non-bound phage. The bound population of phage is replicated on a lawn of host bacteria; and the protein is detected by observing bacterial cell lysis.

Another approach to biomolecule detection involves the detection of biomolecular complexes. Accordingly, one method is practiced by providing a support having disposed thereon a first biomolecule and contacting the first biomolecule with a second biomolecule under conditions that promote the formation of a complex comprising the first biomolecule and the second biomolecule. Next, the complex is contacted with a collection of phage, wherein individual phage in the collection have a protein that binds to the second biomolecule and, wherein contact of the second biomolecule and the collection of phage results in a non-bound population of phage and a bound population of phage. Subsequently, the non-bound population of phage are removed in a manner that retains the bound population of phage and the bound population of phage is placed together with a host for the phage under conditions that permit the bound phage to infect the host so as to produce a replicated population of phage. Detection of the replicated population of phage is a measure of the presence and location of the first biomolecule.

In several aspects of this embodiment, the phage express or are joined to avidin or strepavidin or a derivative thereof or a sequence that binds an antibody. The first biomolecule can be selected from the group consisting of a lipid, a carbohydrate, a protein, and a nucleic acid. The first biomolecule can be separated by a one-dimensional or a two-dimensional procedure and the support can be selected from the group consisting of a gel, a membrane, a filter, a paper, a chromatography matrix, and a chromatography resin. In some aspects, the gel has a plastic backing. Preferably, a suspension of phage is contacted with the second biomolecule and the unbound population of phage is removed by washing with a buffer. The phage suspension and washing buffer can contain blocking agents including but not limited to, casein, nonfat milk, bovine serum albumin, gelatin, tRNA, and a non-ionic detergent (e.g. Tween or NP-40) to reduce nonspecific binding and facilitate removal of non-bound phage. The bound population of phage is replicated on a lawn of host bacteria; and the protein is detected by observing bacterial cell lysis.

In another embodiment, a method of determining whether a target biomolecule is present in a biological sample is provided. This approach is conducted by providing a support having disposed thereon a biological sample that can have a target biomolecule, contacting the biological sample with phage, which has disposed on its outer surface a binding protein specific for the target biomolecule, under conditions suitable to permit the phage to bind to any of the target biomolecule that is present in the sample thereby resulting in a bound population of phage. Subsequently, the bound population of phage is placed together with a host for the phage under conditions that permit the bound phage to infect the host so as to produce a replicated population of phage and the replicated phage are detected whereby the presence of the target biomolecule in the biological sample is determined.

In several aspects of this embodiment, the target biomolecule is selected from the group consisting of a lipid, a carbohydrate, a protein, and a nucleic acid and the target biomolecule can be separated by a one-dimensional or a two-dimensional procedure. The support is selected from the group consisting of a gel, a membrane, a filter, a paper, a chromatography matrix, and a chromatography resin and the gel can have a plastic backing. Preferably, a suspension of phage is contacted with the biological sample and the unbound population of phage is removed by washing with a buffer. The phage suspension and washing buffer can contain blocking agents including but not limited to, casein, nonfat milk, bovine serum albumin, gelatin, tRNA, and a non-ionic detergent (e.g. Tween or NP-40) to reduce nonspecific binding and facilitate removal of non-bound phage. The bound population of phage are replicated on a lawn of host bacteria and the protein is detected by observing bacterial cell lysis. Additionally, the approach detailed above can include isolating at least one phage from the replicated population of phage and incorporating the phage into a biotechnological tool, a diagnostic reagent or a pharmaceutical.

In another embodiment, a phage comprising a nucleic acid attached to a protein expressed by the phage is contemplated. This embodiment can also have a phage comprising a linker that joins the nucleic acid to the protein expressed by the phage. The nucleic acid can comprise biotin and the phage can express avidin, strepavidin, or an analogue thereof. Other embodiments concern biomolecular complexes. One such complex, has a target nucleic acid joined to probe nucleic acid that is itself joined to a phage through a protein (e.g., avidin, streptavidin, or a derivative thereof). This complex can also include a bacterial cell joined to the phage.

In another embodiment, a method of identifying a nucleic acid is provided whereby the biomolecular complex described above is detected. Still further, a method of identifying a polymorphism in a subject is contemplated in which a biological sample having polynucleotides is obtained from the subject and the complex described above is detected in the biological sample.

DETAILED DESCRIPTION OF THE INVENTION

Figure 1:
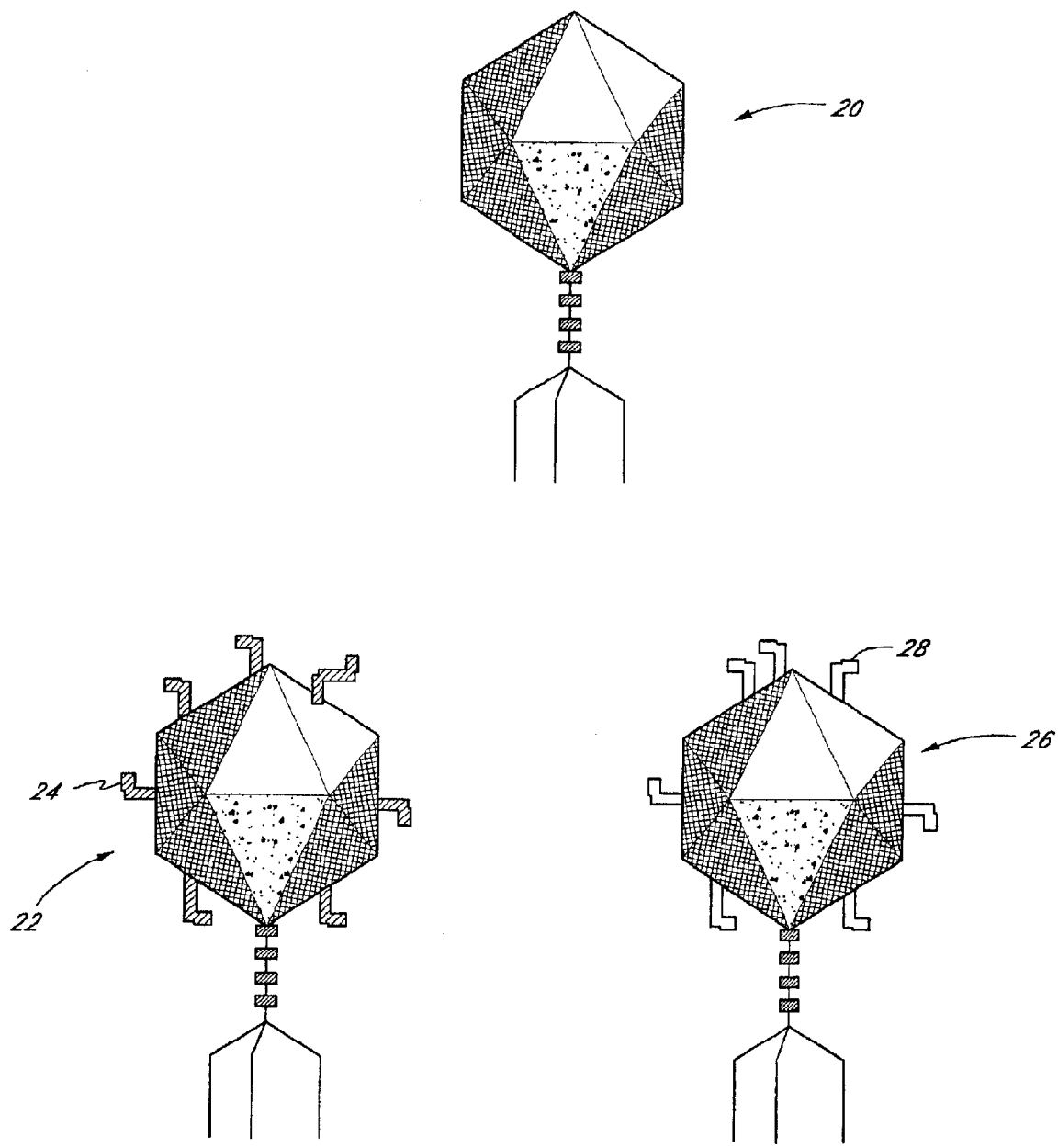
FIG. 1 illustrates a representation of a wild-type phage and a phage with a specific ligand or antibody domain displayed on its surface.

A highly sensitive biomolecule detection system and methods of use of the foregoing has been discovered. In several embodiments, the exponential growth of a cell is used as a marker by which the presence and location of a specific target biomolecule disposed on a support is determined. In other embodiments, the exponential amplification of a virus infecting a cell is used as a marker by which the presence, location, and identification of a specific target biomolecule disposed on a support is determined. By using, bacteria, yeast, or bacteriophage, for example, each having a probe biomolecule that interacts with a target biomolecule, the presence of the target biomolecule can be identified efficiently and with a high degree of sensitivity by detecting the propagation of the organism at a location that corresponds to the position of the target biomolecule on the support. The embodiments described herein have biotechnological application and many can be incorporated into diagnostic protocols and kits, as well as, pharmaceuticals and treatment protocols.

By genetic engineering or the manipulation of cells or virus, virtually any probe biomolecule can be expressed or joined to the cell or virus. For example, cells or virus having avidin, streptavidin or a derivative thereof on their surface can be attached to a biotinylated nucleic acid. Additionally, a heterofunctional antibody having one domain that binds to avidin, streptavidin, or a derivative thereof and a second antibody domain that is already bound to a carbohydrate or a lipid can be joined to a cell or virus. Further, a cell or virus can display or present on their cell surface several different probe biomolecules simultaneously so as to provide an agent that can interact with a multitude of target biomolecules. The expression of multiple cell surface proteins and/or the use of several different types of heterofunctional antibodies that recognize different epitopes on the cell or viral surface and different ligands for display are contemplated.

Accordingly, many different "probe biomolecules" that interact with a specific "target biomolecules" can be presented or displayed on a cell or viral surface and these organisms can be used to identify the presence and location of minute quantities of a target biomolecule by virtue of cell or viral propagation. For example, target biomolecules (e.g., lipids, carbohydrates, proteins, and nucleic acids) disposed on a support can be detected by using a bacteria, yeast, or bacteriophage that expresses a probe biomolecule that interacts with the target biomolecule or by using a bacteria, yeast, or bacteriophage having a probe biomolecule attached to the surface of the organism.

By one approach, a suspension of bacteria or yeast that display a probe biomolecule (either by expression or attachment to the cell surface) are applied to a support having a target biomolecule disposed thereon. In some embodiments, a dot blot manifold apparatus is used and the cells are applied under mild vacuum. The cells are allowed to attach to the target biomolecule for a sufficient time. Next, the unbound and non-specifically bound cells are washed from the support by applying a suitable buffer or growth media. The cell suspension and washing buffer can contain blocking agents including but not limited to, casein, nonfat milk, bovine serum albumin, gelatin, tRNA, and a non-ionic detergent (e.g. Tween or NP-40) to reduce nonspecific binding and facilitate removal of non-bound cells.

Subsequently, the cells that remain bound to the target biomolecule on the support are contacted with a second support having nutrients sufficient to promote growth of the cells (e.g., an agar plate). The agar plate is incubated overnight, the support with bound cells is desirably retained with the agar plate, so as to promote the exponential growth of the bacteria. Colonies of cells will appear at sites that mirror image the position of the target biomolecule on the support. In this manner, the presence and location of the target biomolecule are identified by the exponential growth of the cells.

Preferably, the exponential growth of bacteriophage is used to identify the presence and location of a target biomolecule. A "bacteriophage" or "phage" is a virus that can infect and grow inside of a bacterial host cell. "Phage libraries" are collections of cloned virus particles containing DNA that represents all of the genetic information needed to produce an identical copy of the virus particle. Phage can also be made to express a binding protein that is "displayed" on the surface of individual phage particles. These binding proteins can be made such that they can interact with any desired target biomolecule (e.g., a lipid, carbohydrate, nucleic acid, peptide, or chemical). In some contexts, the term "display" also refers to the presentation of a binding molecule, such as a nucleic acid, that is attached to the surface of a phage in a manner that permits the attached binding molecule to interact with the target biomolecule. Thus, "phage-display libraries" are composed of a collection of phage, wherein individual phage express a protein that binds to a target biomolecule or a collection of phage, wherein individual phage have an attached binding molecule that interacts with the target biomolecule.

When a single phage particle from a library of particles comes into contact with a bacterium, the phage chromosome is transferred to the bacterium where it initiates a genetic program that results in the production of more phage particles. As phage infection proceeds, there can be produced many millions of progeny phage produced from a single starting phage. In this way it is possible to "amplify" or "propagate" the phage. Phage infection results in bacterial cell lysis and, as amplification proceeds, a clear zone or "plaque" appears on the bacterial lawn. The presence of a plaque on a bacterial lawn, thus, "marks" the presence and location of infective phage. Phage can then be removed from the plaque and used to infect other bacteria or DNA from the phage can be isolated, manipulated, and cloned into cells so as to express a desired protein. This process of isolating phage DNA, manipulating it, and cloning it into cells for the expression of proteins is referred to as "phage-subcloning".

Figure 2:
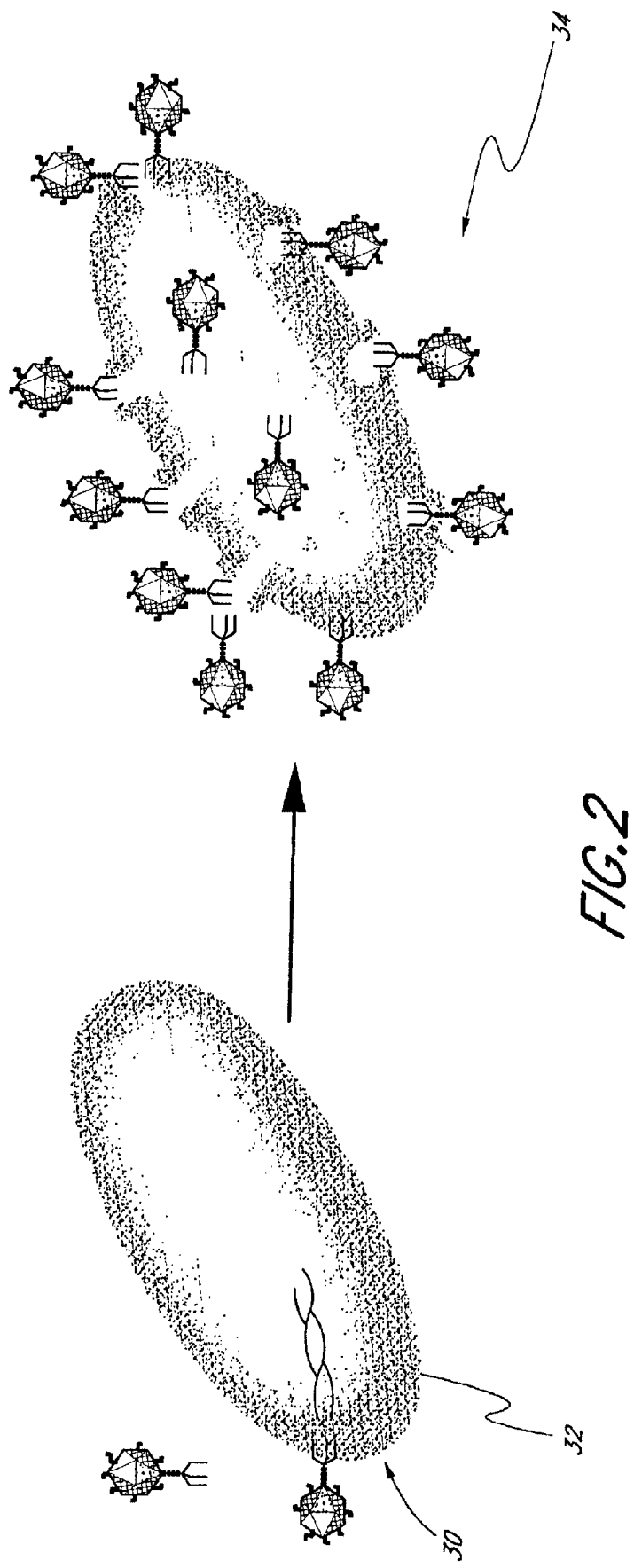
FIG. 2 illustrates phage infecting a bacterium and the exponential amplification that results from the infection.

Many embodiments concern the discovery that phage display can be exploited for general and specific detection of target biomolecules disposed on a support. Referring to FIG. 1, a wild-type phage (20), a phage displaying a ligand (22), and a phage displaying an antibody domain (26) are illustrated. The "display" of a ligand (24) or an antibody domain (28) on the surface of phage enables the virus to bind to a target biomolecule that is disposed on a support (36). Phage display libraries having phage that express a ligand (22) or phage that express an antibody domain (26) can then be exponentially amplified by infecting appropriate host bacteria, as shown in FIG. 2. During infection (30), phage attach to a bacterium and inject their DNA (32) and phage replication results in cell lysis (34). The appearance and location of plaques mark the presence and location of the target biomolecule.

Figure 3:
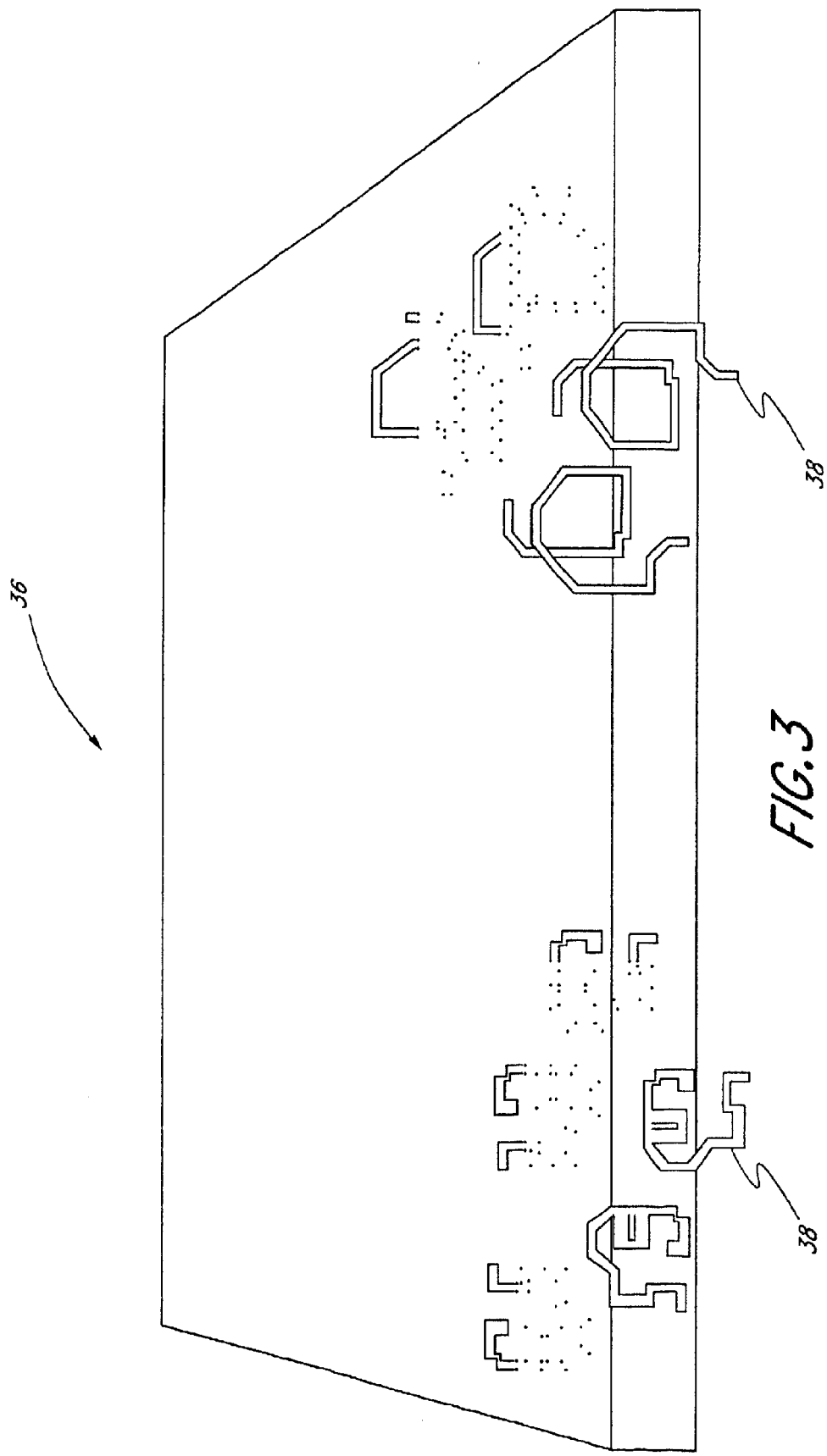
FIG. 3 is a representation of protein in a gel that has been separated by two-dimensional gel electrophoresis.
Figure 4:
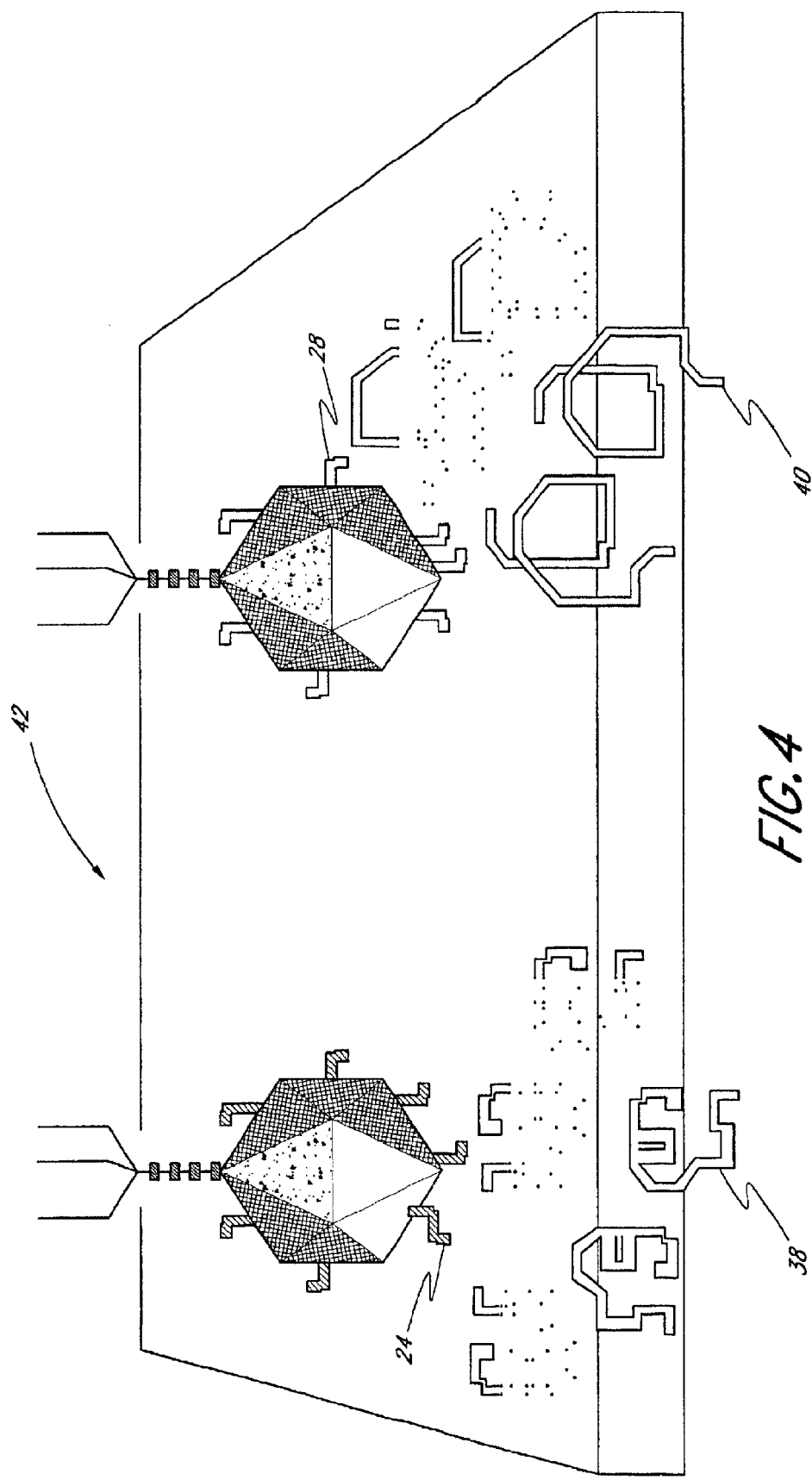
FIG. 4 illustrates phage having a specific ligand or antibody domain displayed on its surface bound to protein in a gel that has been separated by two-dimensional gel electrophoresis.

The target biomolecule (38) can be disposed on various types of supports (36) prior to contact with phage. By one approach, illustrated in FIGS. 3 and 4, a protein (38) is separated on a high resolution two-dimensional electrophoretogram (36) and then is exposed to phage from a phage display library, which have a ligand (24) or an antibody domain (28) specific for the separated protein (38) that is displayed on the surface of the phage. In other embodiments, the protein (38) is transferred to a blotting membrane (36) prior to contact with the phage. Still more embodiments involve blotting the protein (38) to a support (36) (e.g., blotting membrane) using a dot blot apparatus or separating the protein (38) on a thin-layer chromatography matrix (36) prior to contacting the protein (38) with the phage.

Figure 5:
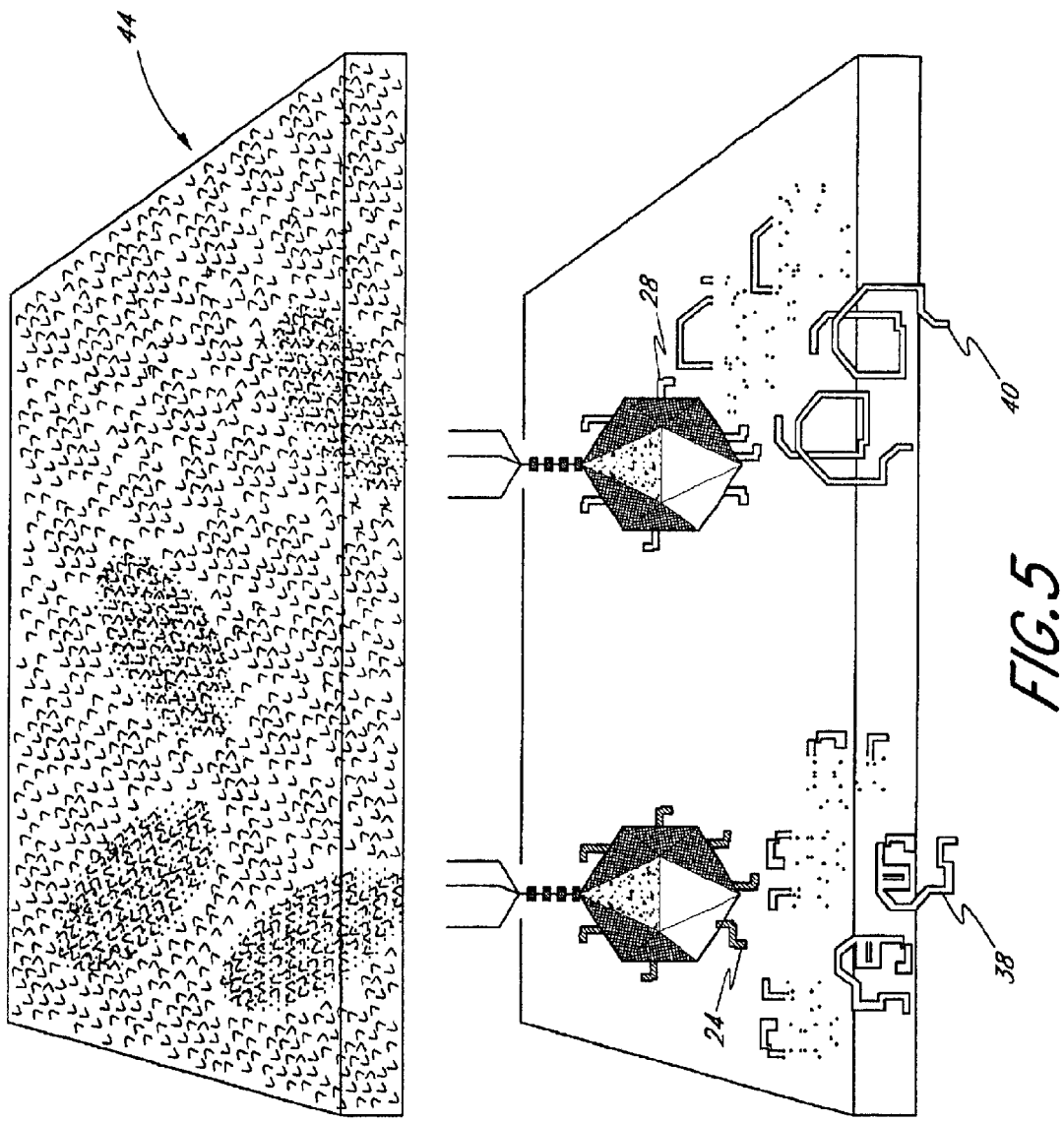
FIG. 5 illustrates a replicate plating of phage bound to protein in a gel.
Figure 6:
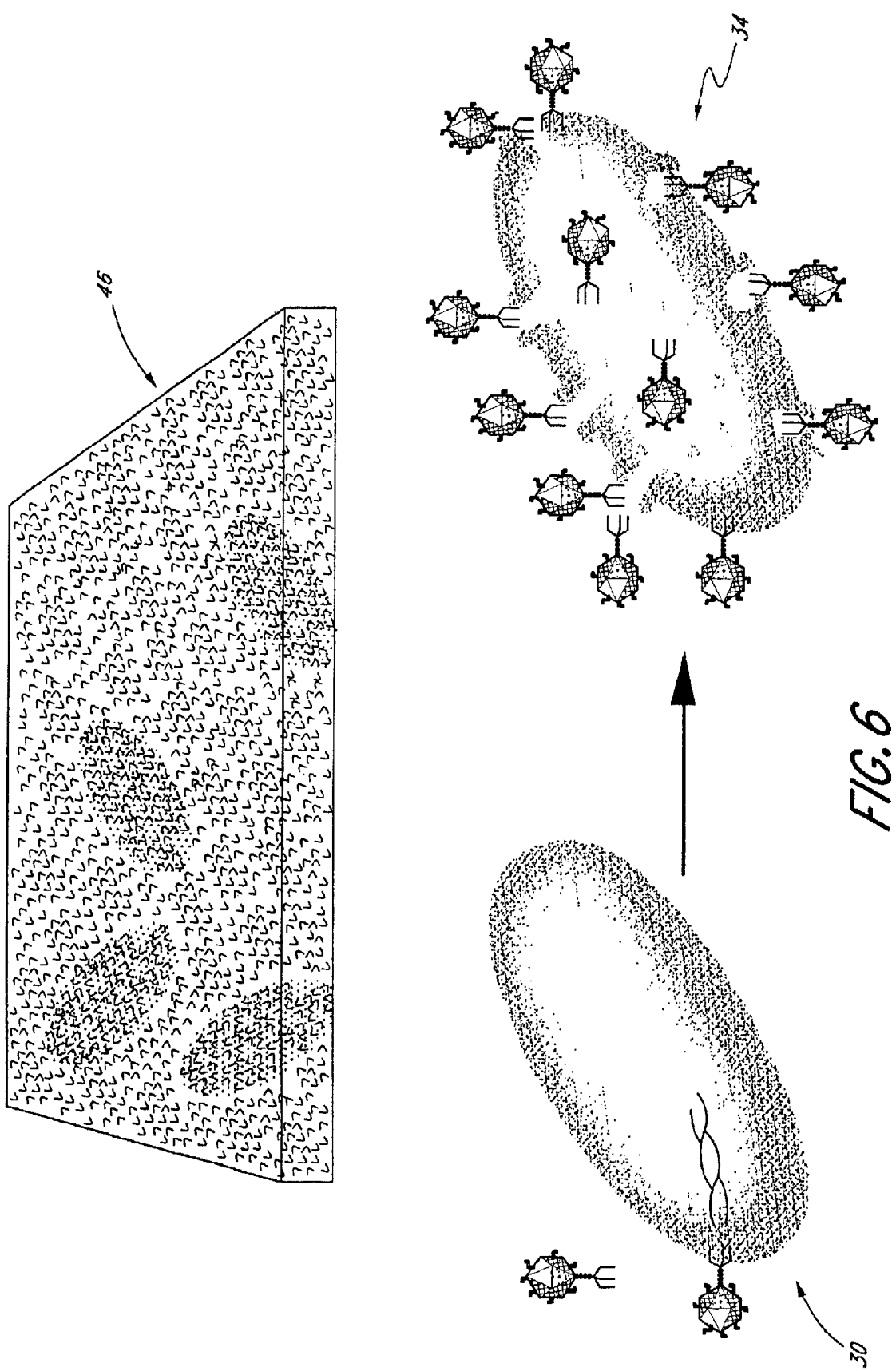
FIG. 6 depicts the infection of bacteria on a bacterial lawn by phage that were bound to proteins separated on a gel by two-dimensional gel electrophoresis.

Subsequent to binding of the phage, the electrophoretic gel (36), for example, which contains the protein-bound phage, is washed with buffer to remove residual non-bound phage and non-specifically bound phage. FIG. 5. The phage suspension and washing buffer can contain blocking agents including, but not limited to, casein, nonfat milk, bovine serum albumin, gelatin, tRNA, and a non-ionic detergent (e.g. Tween or NP-40) to reduce non-specific binding and facilitate removal of non-bound phage. Once washing is complete, the support-bound phage are replicate plated on an appropriate bacterial host lawn (44). Following a short contact period (~10 minutes) the plate containing the infected bacterial lawn (46) is incubated overnight. FIG. 6.

Figure 7:
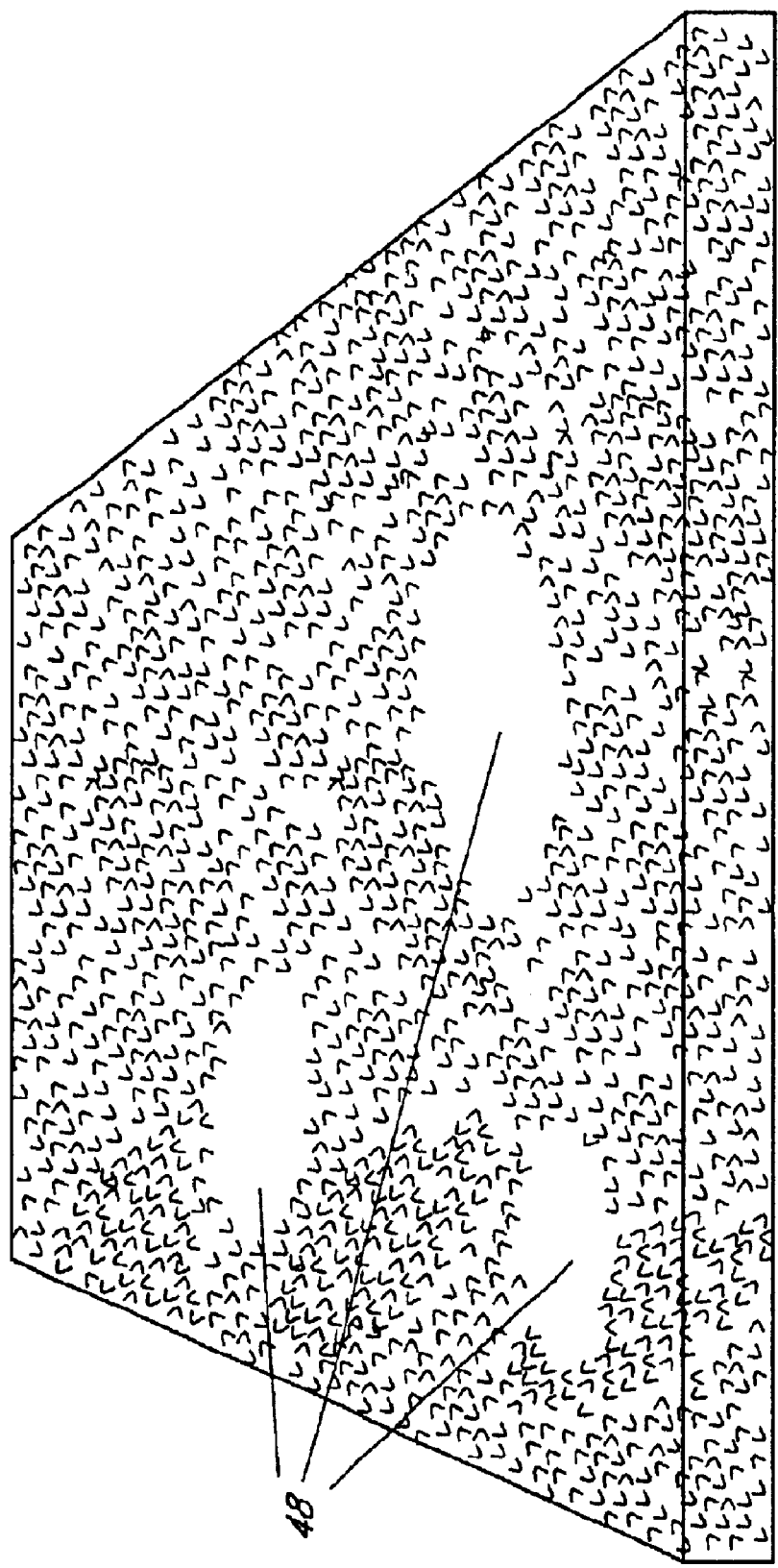
FIG. 7 illustrates plaques on a bacterial lawn that result from phage infection initiated by the phage bound to proteins in a gel.
Figure 8:
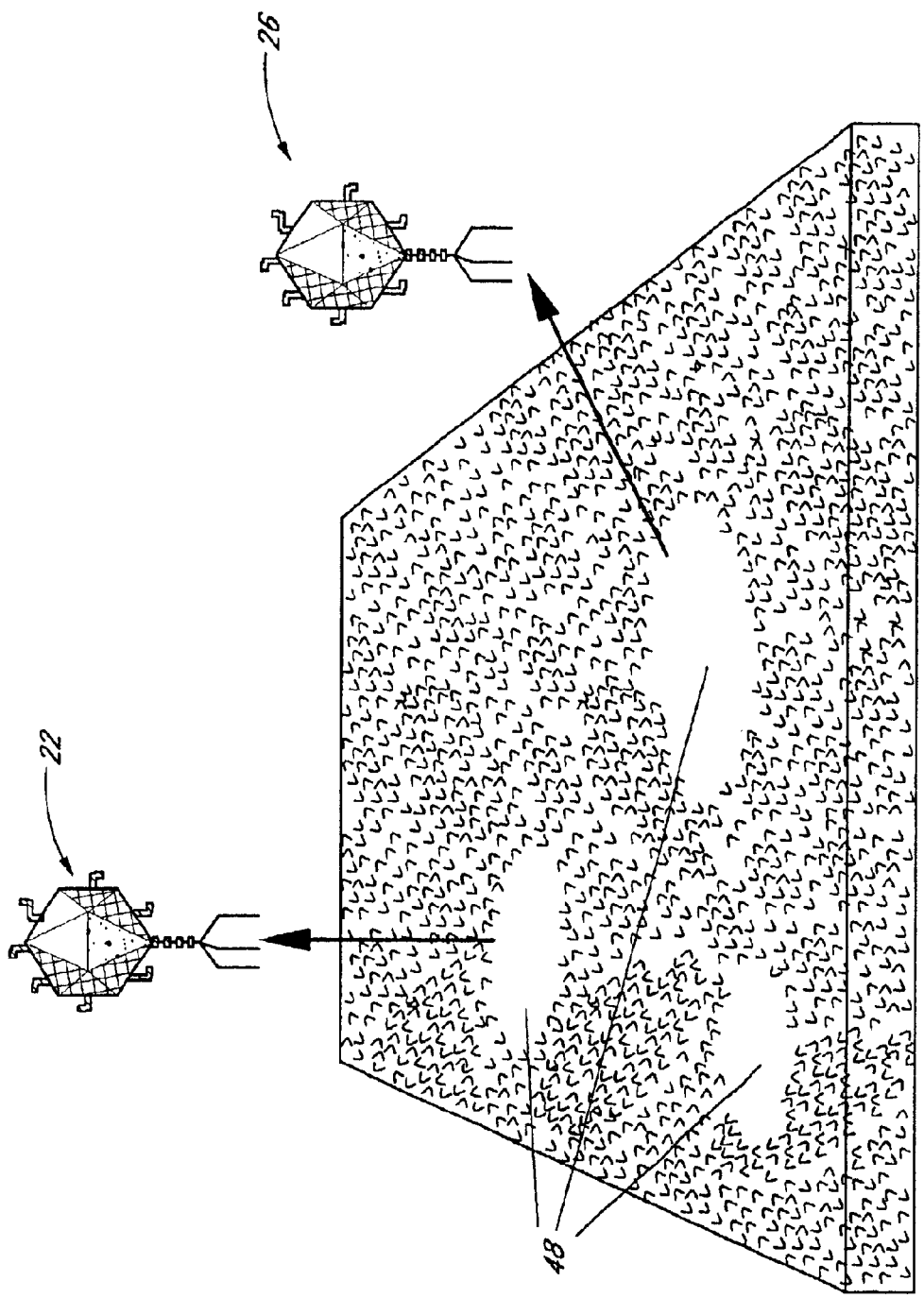
FIG. 8 illustrates the isolation of phage having a ligand or antibody domain displayed on their surface from the plaques that result from phage infection initiated by the phage bound to proteins in a gel.

Phage that successfully infect the host bacteria will undergo exponential growth. The multiplying phage and lysis of bacteria results in appearance of plaques (48) on the bacterial lawn (44). FIG. 7. These plaques indicate the position of the proteins (38) on the electrophoretic gel (36). Furthermore, each plaque contains phage that display a ligand (22) or an antibody domain (26) that permits specific binding to a specific protein (38) located on the gel (36). As illustrated in FIG. 8, these phage can be isolated, cultured, and can be used for further purification and characterization of specific proteins (38) or in diagnostics or therapeutics. The section below describes several types of supports and many approaches that can be used to dispose biomolecules on a support.

Disposing the biomolecule on a support

There can be many advantages for separating a desired biomolecule from contaminating biomolecules present in a biological sample prior to performing the detection technique described herein. Notably, the separation of the desired biomolecule can facilitate the isolation of the biomolecule after identification. A great many biomolecule separation techniques, which can be used prior to disposing a desired biomolecule on a support or can be used to simultaneously separate and dispose the biomolecule on a support, are available. The separation of the desired biomolecule from others in the sample is not necessary, however, to practice the invention.

Target biomolecules can be separated from contaminating biomolecules by a one-dimensional or two-dimensional procedure, for example. (See e.g., *Methods in Enzymology* Vol. 182, Guide to Protein Purification, ed. Deutscher, Academic Press Inc. pp. 425–477, San Diego, Calif. (1990), *Current Protocols in Molecular Biology*, Ausubel et al., ed., John Wiley & Sons (1994–1998), and Sambrook et al., *Molecular Cloning: A Laboratory Manual,* 2ed. Cold Spring Harbor Laboratory, Cold Spring Harbor, N.Y. (1989)). Denaturing and non-denaturing gel electrophoresis can be used to separate nucleic acids and sodium dodecyl sulfate-polyacrylamide gel electrophoresis (SDS-Page) is a common method to separate proteins. Further, pulse-field electrophoresis, two-dimensional protein electrophoresis, isoelectric focussing, and other separation techniques are contemplated for use with embodiments. Additionally, biomolecules can be separated chromatographically, for example, by thin layer chromatography (TLC) or liquid chromatography techniques, such as high performance liquid chromatography (HPLC) or fast performance liquid chromatography (FPLC), or by affinity chromatography techniques.

Another common laboratory technique called "blotting" can also be used to dispose a biomolecule on a support. This technique allows for the transfer of separated biomolecules on a matrix to a solid membrane or a filter. (See e.g., *Current Protocols in Molecular Biology*, Ausubel et al., ed., John Wiley & Sons (1994–1998), and Sambrook et al., *Molecular Cloning: A Laboratory Manual,* 2ed. Cold Spring Harbor Laboratory, Cold Spring Harbor, N.Y. (1989)). Advantageously, biomolecules disposed on a membrane support by blotting can be immobilized or fixed into position so that further rounds of detection with a new library of phage that display a different binding molecule can be accomplished. By "stripping" or removing the first bound phage, by techniques known in the art, subsequent rounds of detection with new probes (i.e., new phage libraries displaying new binding molecules) can be performed.

The term "matrix" or "support" refers to a carrier, a resin or any macromolecular structure used to attach, immobilize, or dispose thereon a biomolecule such as a lipid, nucleic acid, or protein. The support can have a hydrophobic surface that interacts with the biomolecule or the surface can be charged, for example, a charged nitrocellulose or nylon membrane. The support can be of many shapes and sizes so long as the shape and/or size does not prevent the phage from binding to the biomolecule disposed on the support and/or prevent bound phage from infecting bacteria. Desirable supports, for example, include polyacrylamide gels, agarose gels, composite gels, or other gel matrices, papers, membranes including nitrocellulose and nylon membranes, and chromatography matrices, as used in thin layer chromatography, and affinity chromatography. The term "support" can also refer in some contexts to a structure that has sufficient nutrients to sustain cell growth (e.g., agar plates). The section below describes the use of phage display libraries in greater detail.

Phage display libraries

Many types of phage can be used in a phage display library, including but not limited to, lamboid phage, such as λ, T phage, such as T4 and T7, and filamentous phage, such as M13. The manufacture of several different types of phage libraries that display proteins that bind to biomolecules have been described. (See eg., U.S. Pat. Nos. 5,702,892 and 5,824,520 to Mulligan-Kehoe, U.S. Pat. No. 5,223,409 to Ladner, et al., European Patent Application EP844,306A1 to McCafferty et al., Chester et al., *Br. J. Cancer* 69 (Suppl. 21):15 (1994), Hagag et al., *Anal Biochem.* 191:235 (1990), Merz et al., *J. Neurosci. Methods* 62:213 (1995), Nissim et al., *EMBO J.* 13:692 (1994), Watkins et al., *Anal. Biochem.* 256:169 (1998), Flower et al., *Abstracts of the 95$^{th}$ General Meeting of the American Society for Microbiology*, page 575 (1995), Geoffroy, et al., *Gene* 151:109 (1994), Chang et al., *J. Immunol* 147:3610 (1991), Kuwabara et al., *Nature Biotechnology* 15:74 (1997), and Mikawa et al., *J. Mol. Biol.* 262:21 (1996)). Collections of phage that express a binding protein can also have linkers attached to the binding protein (e.g., "λ linkers" corresponding to the flexible arms of 8 phage) so as to create a flexible binding domain that does not sterically interfere with the ability of the phage to infect a bacteria or hybridize with or bind to the target biomolecule.

In one embodiment, a 8 phage expression library is created substantially as described by Mikawa et al., *J. Mol. Biol.* 262:21 (1996), wherein a protein that interacts with a target biomolecule is expressed on the surface of the phage. The 8 phage are preferably constructed so that the binding protein replaces the D protein or is expressed as a fusion protein with the D protein of the 8 protein coat. The following example describes several methods to construct D fusion vectors.

EXAMPLE 1

In order to modify the 5' end of the D gene, a pair of oligonucleotide primers, 5'-GGATCCGGGGGTAT-TAATATGACGGGTACCAGCAAAGAAACCTTTACC- (SEQ. ID. No. 1) and 5'-ATCGGCCGGTCGACTTAAAC-GATGCTGATTGC (SEQ. ID. No. 2), are used for PCR amplification of the gene using λ1685 DNA as a template. (Saiki et al., *Science,* 239:487 (1988)). The former primer contains the ribosome-binding site of the *S. aureus* protein A gene. (Uhlén et al., *J. Bio. Chem,* 259:1695 (1984)). The PCR fragment digested with BamHI and EagI is cloned between BamHI and EagI of pACYC184, resulting in pλD1.

Separately from the above construction, a 4587 bp BamHI-ApaI fragment of λ1685 DNA encompassing the genes 'C, 'Nu3, D, E, FI, FII, Z, U, V and G' is also cloned into pUM15 for the mutagenesis of the D gene, resulting in pλDo. The pUM15 plasmid is a derivative of pUM13 and has ApaI and BamHI sites in the multiple cloning site (MCS). (Maruyama & Brenner, *Gene,* 120:135 (1992)). In order to create a unique SfiI site between the second and third codons of the D gene, two pairs of oligonucleotide primers, 5'-CCGGGGATCCTCAACTGTGAGGA (SEQ. ID. No. 3) and 5'-ATGGCCCCGGGGGCCGTCATAAACATCCCTTACA-CTG (SEQ. ID. No. 4), and 5'-TTGGCCCCCG- GGGC-CAGCAAAGAAACCTTTACCCATTA (SEQ. ID. No. 5) and 5'TGCCCTTAAGCACGGCAGAAACT (SEQ. ID. No. 6), are used for PCR amplification of the gene. To create pλDs, the two PCR fragments are digested with BamHI and SfiI, and SfiI and AfAI, respectively, and are cloned in tandem between the BamHI and AfAI sites of pλDo. After eliminating all the remaining MCS of pUM15, a new MCS cassette encoding HindIII, SphI, PstI, AccI, HincII, XbaI, BamHI SmaI, KpnI, SacI, EcoRI and HaeIII are introduced into the unique SfiI site located at the 5' end of the D gene on pλDs, resulting in pλDa. In some embodiments, a synthetic cassette encoding a collagenase recognition sequence (Germino & Bastia, *Proc. Natl Acad. Sci USA*, 81:4692 (1984)), factor Xa recognition sequence (Maina et al., *Gene*, 74:365 (1988)) and linker sequence can be cloned in the KpnI and SfiI sites in PλDa to create a plasmid pλDb. The plasmids described above are used for the fusion of desired binding protein to the N terminus of gpD.

After confirming that the fusion proteins are functionally active and are incorporated into the phage particle, the pλD5 vector is constructed by the following procedures. The linker sequence of λfoo is amplified by PCR with primers, 5'-GAATTCAGCGGCCGCATAGCCGACCGGGCCAAA-TTCTATCGAAGGTCGTGGGACTCCGACCCCG-ACCACTCCC (SEQ. ID. No. 7) and 5'-AATGGCCCCGGGGGCCGTAATCATGGTCATAGC (SEQ. ID. No. 8). (Maruyama et al., *Proc. Natl. Acad Sci. USA*, 91:8273 (1994)). The former primer contains a NotI site, amber stop codon and endopeptidase recognition sequence. After digesting with EcoRI and SfiI, the PCR fragment is cloned into pλDa to produce pλDα. A fragment containing the modified D gene is cut out with PstI and PvuII from pλDα and is cloned with the PstI and SmaI sites in pBSC to make pλD5.

For construction of plasmid vectors for the C-terminal fusion of gpD, NheI and EagI sites are introduced between the D and E genes by PCR using two pairs of oligonucleotide primers, 5'-CCGGGGATCCTCAACTGTGAGGA (SEQ. ID. No. 3) and 5'-AACGGCCGAATGCTA-GCGATAACGATGCTGATTGCCGTTCCGGC (SEQ. ID. No. 9), and 5'-AACGGCCGCTTTACCCTTCATCAC-TAAAG (SEQ. ID. No. 10) and 5'-TGCCCTTAAGCACG-GCAGAAACT (SEQ. ID. No. 11), and λ1685 as a template. The two PCR fragments are digested with BamHI and EagI, and EagI and AfAI, respectively, and are cloned in tandem between the BamHI and AfAI sites in pλDo to create pλDne. The D gene ochre termination codon, TAA, is replaced with an amber termination codon, TAG, in pλDne. DNA encoding a collagenase recognition sequence, peptide linker, MCS and lacZ' is amplified by PCR from λfoo DNA, using primers, 5'AAGCTAGCAGCTGGCCTGTTGGGCCCACT (SEQ. ID. No. 12) and 5'-AACGGCCGCTATCTATCTA-GAATTCGAGCTCGGTACCCGGG (SEQ. ID. No. 13). This PCR fragment is digested with NheI and EagI, and is cloned between the NbeI and EagI sites in pλDne, resulting in plasmid pλDβ. A D gene fragment is also isolated from pλDne with BamHI and EagI and is cloned into BamHI and EagI in pBSC. By eliminating the MCS between KpnI and BamHI in pBSC, pλD is created. The PCR fragment encoding a collagenase recognition sequence, peptide linker, MCS and lacZ', is inserted into NheI and EagI in pλD to make pλD3.

All oligonucleotide primers mentioned above can be synthesized using an Applied Biosystem DNA synthesizer model 394. The sequences of all PCR products are preferably, confirmed by DNA sequencing (Sanger et al., *Proc. Natl. Acad. Sci. USA*, 74:5463 (1977)), since PCR induces mutations at a high rate (Maruyama, *Technique*, 2:302 (1990); Williams & Winter, *Eur. J. Immunol*, 23:1456 (1993)).

A 4755 bp ApaI-ApaLI fragment of pλDα and a 4950 bp ApaI-ApaLI fragment of pλDβ are cut out with ApaI and ApaLI, and are ligated with left and right arms purified from λfoo DNA digested with ApaI and ApaLI to make phage vectors, λfooDn and λfooDc, respectively. In vitro packaging of the ligated DNAs are carried out by conventional techniques. (Maruyama et al., *Proc. Natl. Acad Sci. USA*, 91:8273 (1994)). By using the teaching described in this example, a D fusion vector can be manufactured. The next example describes an approach to clone a binding protein into a 8 phage vector.

EXAMPLE 2

In one embodiment, plasmid pRIT5 is used as a template for PCR to amplify a DNA fragment encoding the IgG-binding domains of protein A, using primers 5'-TTCTGCAGCGCGCAACACGATGAAGCTCAA (SEQ. ID. No. 14) and 5'-TTGGTACCGCTCACCGAAG-GATCGTC (SEQ. ID. No. 15). The PCR fragment encoding the domains E, D, A and B is digested with PstI and KpnI, and is inserted into the PstI and KpnI sites of pλDb to fuse the domains to the N terminus of gpD. To produce the protein A-gpD fusion protein in bacteria, the fragment encoding the protein A-gpD fusion is cut out with PstI and PvuII, and is cloned with the PstI and SmaI sites of pBSC. The resulting construct is designated pλAD, in which expression of the fusion protein is placed under the control of the lac promoter. A DNA fragment encoding the B domain of protein A is cut out with HindIII and EcoRI from pλAD and is cloned into the HindIII and EcoRI sites of pλD3, resulting in plasmid pλDA. pAD, a deletion derivative of pλDA, is then made by eliminating a 465 bp HindIII fragment encoding the IgG-binding domains E, D and A of protein A.

For the construction of pλPAn, the protein A gene is isolated from pλAD by digestion with HindIII and EcoRI, and is cloned into the HindIII and EcoRI sites of λfooDn. Similarly, λPAc is constructed from a HindIII-EcoRI fragment of pλAD and λfooDc digested with HindIII and EcoRI.

The teachings of this example can be used to construct 8 D expression vectors that encode a desired binding protein on the surface of 8 phage. By inserting a Hind III and EcoRI site flanking a DNA encoding a desired binding protein (e.g., synthetic DNA encoding a binding domain for an antibody with flanking Hind III and EcoRI sites), a 8 D expression vector that expresses a desired protein on the surface of 8 phage can be rapidly manufactured. The next section describes more approaches to manufacture phage that display a desired binding molecule.

The display of binding molecules attached to phage

In several embodiments, a phage display library is created by attaching a binding molecule, such as a nucleic acid or peptide, to the phage. Several methods to attach nucleic acids and peptides to other proteins are known in the art. Preferred approaches include the attachment of binding molecules through disulfide bonds, chemically modifiable linkers, and biotin-avidin interactions. Thus, some phage display libraries described for use herein do not express a binding protein specific for a target but rather have a binding molecule attached to the surface of the virus in a manner that does not perturb viral infectivity or the ability to interact with a target biomolecule.

In one embodiment, for example, a nucleic acid probe can be attached to the surface of a phage through chemical modification of the proteins of the coat of the phage. Preferably, however, a phage expressing avidin or strepavidin or an analouge thereof is attached to a biotinylated nucleic acid probe. Flexible linkers, such as λ linkers that comprise amino acid sequences that encode arms of the 8 virus, can also be used so that the nucleic acid probe does not sterically interfere with the ability of the phage to infect a bacteria or hybridize with a target nucleic acid. Phage display libraries that comprise identifiable markers are described in the next section.

Phage display libraries having identifiable markers

In some embodiments, phage have a marker that facilitates plaque identification. The β-galactosidase gene, for example, can be incorporated into phage so that when a suitable host that lacks β-galactosidase is infected with the modified phage, the introduction of the β-galactosidase exon (LacZ) into the host by the phage permits the cell to synthesize β-galactosidase in the presence of an inducer such as IPTG (isopropylthio-β-galactoside). (Kizer and Brock, *Gene Probes*, M. Conn ed. Academic Press (1989)). Thus, phage grown on a bacterial lawn will produce blue plaques in the presence of IPTG and the indicator substrate Xgal (5-bromo-4-chloro-3-indolyl-β-D-galactoside).

Many other markers are known to those of skill in the art and their use would be apparent given the this disclosure. The marker can be a gene that is expressed by the phage or the host when infected by the phage. The marker can be a composition, such as a protein, chemical, radioactive, or fluorescent moiety attached to the phage. Suitable markers include, but are not limited to, green fluorescent protein (GFP), digoxigenin, fluorescent compounds, magnetic compounds, and radioactive particles. The section below describes the binding of phage to the target biomolecule and the removal of non-bound and non-specifically bound phage.

Binding of the phage to the target biomolecule and removing unbound and non-specifically bound phage Once the target biomolecule is disposed on a support, the target biomolecule is brought in contact with phage from a phage display library. There can be many ways to bring the phage in contact with the target protein. Preferably, the support having the target biomolecule is provided a phage suspension. The phage suspension can be applied under vacuum (e.g., using a dot blot manifold) or the support can be immersed in a phage-containing solution. The concentration of phage in the phage suspension can be from between $10^2$ pfu/ml to $10^{12}$ pfu/ml and desirably $10^7$ pfu/ml to $10^{11}$ pfu/ml and preferably $10^8$ pfu/ml to $10^{10}$ pfu/ml. Depending on the binding kinetics of a particular phage and phage-display library, greater or less concentrated suspension of phage can be used. Although titration of the concentration of the phage suspension is desirable for some embodiments, it is not necessary.

In some cases, the biomolecule disposed on the support is "fixed" or immobilized to the support so that the binding and washing phases do not remove the biomolecule from the support. The fixation of protein in a gel and the immobilization of nucleic acids to a membrane, for example, are routine in the art of molecular biology. Because of the potential for denaturing proteins present on the phage, prior to the binding phase, supports having fixed or immobilized biomolecules are preferably brought to a suitable buffer for phage binding.

After the phage are allowed to bind to the target biomolecule on the support, washing is performed so that the non-specifically bound phage and unbound phage are removed. Depending on the type of support and manner that the biomolecule was disposed thereon, the buffer used to remove the unbound and non-specifically bound phage can differ. For some embodiments, the buffer can resemble the buffer that composes the gel or separation buffer. In other cases, the buffer that composes the gel or separation buffer can denature proteins of the phage and/or would otherwise be inappropriate. In this case, prior to the binding phase, supports are brought to a suitable buffer, as described above. One suitable buffer can be PBS (phosphate-buffered saline). The phage suspension and washing buffer can also contain blocking agents including, but not limited to, casein, nonfat milk, bovine serum albumin, gelatin, tRNA, and a non-ionic detergent (e.g. Tween or NP-40). The section below describes the propagation of the phage and embodiments that facilitate the determination of phage replication.

Phage replication

Once unbound and non-specifically bound phage have been removed, the phage that are bound to the target biomolecule disposed on the support are replicated in bacteria. Although there can be many ways to replicate phage in bacteria, replicate plating on a bacterial lawn is desirable. By using the replicate plating method, not only can the presence of the protein be rapidly identified but the position of the biomolecule on the support can be resolved.

In other preferred embodiments, the support is brought to a semi-dry state prior to introduction of the bacteria. By one approach, a membrane having phage-bound protein is blotted on absorbent paper prior to applying a suspension of bacteria to the membrane. Additionally, a mild vacuum (e.g., by employing a dot-blot manifold) can be applied to the membrane before, during and after the application of bacterial suspension. The membrane containing protein, phage, and bacteria is then placed on a Luria Broth agar plate (with the bacterial and phage surface on the side away from the agar). Phage amplification and concomitant lysis of the host bacteria results in plaques on the bacterial lawn that mark the positions of the proteins on the support.

Phage from replicated populations of phage (i.e., individual plaques) can also be isolated by conventional techniques and incorporated into diagnostic kits, pharmaceutical products, or biotechnological tools. Phage-subcloning can also be performed so as to generate proteins that specifically interact with the target biomolecule identified by the procedure above. The example below describes embodiments that facilitate replicate plating.

EXAMPLE 3

In one embodiment, a gel having a plastic backing attached is used to facilitate replicate plating. Desirably the plastic backing has tabs, handles, or a gripping means so that replicate plating can be performed precisely. The plastic backing is attached to the gel in a manner that does not interfere with the separation technique. Because many different sizes, shapes, and forms of biomolecule separation devices exist in the art, the size and shape of the plastic backing having an gel attached can be varied. Desirably, separation gels having a plastic backing for replicate plating are packaged in airtight containers and sold as kits.

Accordingly, highly sensitive biomolecule detection using the separation gel with plastic backing is accomplished as follows. A target biomolecule is separated on the gel with plastic backing, the gel is contacted with a phage display library having individual phage that display a binding molecule that interacts with the separated target biomolecule on the gel with plastic backing. Binding is allowed to occur and, subsequently, the non-bound and non-specifically bound population of phage are removed from the gel with plastic backing by washing in a suitable buffer. Replicate plating is performed by gripping the tabs on the plastic backing and contacting the gel surface having the separated target biomolecule and bound phage with a bacterial lawn having a host bacteria for the phage. The gel with a plastic backing and bound phage is then allowed to contact the bacterial lawn for a period sufficient to allow infection. The bacterial lawn is subsequently incubated for a time sufficient to allow amplification of the phage and cell lysis and the presence and location of the separated target biomolecule is detected by the observation of plaques.

In a related embodiment, a bacterial lawn or bacterial culture plate having a plastic backing that facilitates replicate plating is used. Desirably, the plastic backing has tabs, handles, or a gripping means so that replicate plating can be performed precisely. The plastic backing with tabs is attached or is of a one piece construction with an agar plate having a bacterial lawn. Preferably, this embodiment of the bacterial culture plate corresponds in shape and size with the various sizes and shapes of supports used in the field. In some cases, the size and shape of the bacterial culture plate with tabs corresponds to the size and shape of conventional nucleic acid or protein separation gels or membranes. Because many different sizes, shapes, and forms of biomolecule separation devices exist in the art, the size and shape of the bacterial lawn with tabs can be varied. Desirably, replicate plating agar culture dishes having tabs that facilitate replicate plating are packaged in airtight containers and sold as kits that can also have cultures of bacteria and/or phage.

Accordingly, highly sensitive biomolecule detection using the bacterial lawn on the replicate plating agar culture dish having tabs is accomplished as follows. A target biomolecule is separated on a gel that corresponds in shape and size with the replicate plating agar culture dishes having tabs and the gel is contacted with a phage display library having individual phage that display a binding molecule that interacts with the separated target biomolecule. Binding is allowed to occur and, subsequently, the non-bound and non-specifically bound population of phage are removed from the gel by washing in a suitable buffer. Replicate plating is performed by gripping the tabs on the replicate plating agar culture dish with a bacterial lawn and contacting the gel surface having the separated protein and bound phage. The gel and bound phage is then allowed to contact the bacterial lawn for a period sufficient to allow infection. The bacterial lawn is incubated for a time sufficient to allow amplification of the phage and cell lysis and the presence of the separated protein is detected by the observation of plaques. By using the teaching provided in this example, one can manufacture and use a gel apparatus that facilitates the replicate plating step practiced in many of the methods described herein. The section below describes several embodiments that are useful for the detection of nucleic acids disposed on a support.

The detection of nucleic acids disposed on a support

Methods of detecting nucleic acids disposed on a support are also embodiments. As described above, nucleic acids can be disposed and/or separated on many types of supports including, but not limited to, gels, membranes, papers, and chromatography supports. Once the target nucleic acid is disposed on the support, the target is brought into contact with a collection of phage, a phage display library, having individual phage that display a peptide that interacts with a target nucleic acid or a nucleic acid that hybridizes to a target nucleic acid.

Several proteins that bind nucleic acid sequences are known and these proteins or fragments thereof can be expressed or attached to the surface of phage for use in identifying the presence and location of nucleic acids disposed on a support. Proteins that bind specific sequences of nucleic acids include, but are not limited to, DNA or RNA binding proteins, in general and, more specifically, transcriptional proteins, RNA processing proteins, and immunoglobin proteins. For example, immunoglobulin proteins or fragments thereof that bind modified nucleic acids such as biotinylated nucleotides or nucleotides having dinitrophenol (DNP) or isopentenyl-adenosine ($I_6A$) nucleotides can be expressed or attached to the surface of phage so that the detection of a target nucleic acid having these modified nucleotides can be accomplished.

Alternatively, nucleic acid probes can be attached to the surface of phage for use in identifying the presence and location of nucleic acids disposed on a support. A nucleic acid probe can be attached to the surface of a phage through chemical modification of the proteins of the coat of the phage but, preferably, a phage expressing avidin or strepavidin or analogue thereof is attached to a biotinylated nucleic acid probe. Flexible linkers, such as λ linkers, can also be used so that the nucleic acid probe does not stericly interfere with the ability of the phage to infect a bacteria or hybridize with the target nucleic acid. Desirable lengths of linkers can be determined through routine experimentation but are of such a length to allow for attachment of the nucleic acid probe and allow for binding to the target biomolecule and permit infection of a host bacteria.

A phage-nucleic acid reagent (i.e., the phage expressing avidin or strepavidin or an analogue thereof bound to the biotinylated nucleic acid probe) can be first created and then used to hybridize a target nucleic acid disposed on a support. Alternatively, the biotinylated nucleic acid probe can be allowed to hybridize with the target nucleic acid disposed on a support first and, subsequently, the nucleic acid hybrid can be bound with phage expressing avidin or strepavidin or an analogue thereof so as to detect the presence and location of the nucleic acid hybrid. A 5' or 3' biotinylated oligonucleotide can be synthesized by conventional methods and used as the probe nucleic acid or several other methods to incorporate biotin or other modified nucleotides into nucleic acid probes are known. The following example describes another approach to detect a target nucleic acid disposed on a support.

EXAMPLE 4

Although the detection of nucleic acids directly from a gel can be accomplished with an embodiment described herein, the immobilization of a target nucleic acid on a membrane offers the advantage of stripping the blot and re-probing it with another nucleic acid probe or phage-nucleic acid reagent. By one approach, the target nucleic acid is separated on a gel and immobilized to a nylon membrane, according to conventional Southern or Northern techniques, and a biotinylated nucleic acid probe is then contacted with the immobilized target nucleic acid under conditions that allow hybridization. Subsequently, the non-specifically bound hybrids are washed from the membrane and the bound nucleic acid probes are contacted with a phage library expressing avidin or strepavidin or an analogue thereof on the surface of the phage. The strepavidin or avidin-expressing phage are allowed to bind the biotinylated nucleic acid probe attached to the complimentary strand of target nucleic acid and the non-specifically bound phage are removed by washing. The support having the nucleic acid hybrid bound to a phage expressing avidin or strepavidin is then replicate plated to a bacterial lawn. Phage infectivity and cell lysis is then allowed to occur and the presence and location of the target nucleic acid is detected by the observation of a plaque on the bacterial lawn.

Preferably, a biotinylated RNA probe is used with this approach. Biotinylated RNA probes can be manufactured by in vitro transcription in the presence of biotinylated UTP. Additionally, [$^{32}$P] CTP or any other radioactive nucleotide can be incorporated into the in vitro transcription reaction, which allows one to follow a second marker for control or probe purification purposes. Once the biotinylated RNA probe is prepared, a nucleic acid hybridization is conducted.

Accordingly, nucleic acids disposed on a support are brought in contact with the biotinylated RNA probe under conditions that allow hybridization. After a sufficient time for hybridization has passed, RNAse A is added to the hybridization mixture. This enzyme will digest all unhybridized RNA probes and will lower the background signal. After RNAseA digestion, the hybridization is washed several times in an appropriate hybridization wash buffer (e.g., 6xSSC and 7.0% SDS) and then the blot is brought to a buffer suitable for phage attachment (e.g., PBS). The buffer can also contain blocking agents including, but not limited to, casein, nonfat milk, bovine serum albumin, gelatin, tRNA, and a non-ionic detergent (e.g. Tween or NP-40).

Phage that display avidin or streptavidin or a derivative thereof are then contacted to the hybrids for a sufficient time to allow the formation of a nucleic acid-biotinylated RNA probe-phage complex. Subsequently, the non-bound and non-specifically bound phage are removed by washing in a suitable buffer and a suspension of bacteria is provided to the membrane. Infection of the bacteria is allowed to occur and the membrane is brought to a semi-dry state. Next, the membrane having the nucleic acid-biotinylated RNA probe-phage-bacteria complex is applied to a Luria broth agar plate. The appearance and location of plaques on the membrane indicates the presence and location of nucleic acid hybrids on the membrane. By using the teachings described in this example, one can rapidly perform very sensitive nucleic acid hybridizations. The example that follows describes a new approach for in situ hybridization.

EXAMPLE 5

In another embodiment, a highly sensitive method of in situ hybridization is provided. By this approach, a tissue is sectioned and preserved according to conventional techniques, and is subsequently bound with a phage library having phage that display a molecule that binds to a target nucleic acid in the tissue slice. Biotinylated RNA probes that have been hybridized to the target nucleic acid can be used in conjunction with phage displaying avidin, streptavidin, or a derivative thereof, for example. The phage library is contacted with the tissue slice for a period long enough to allow for the phage to bind to the desired target nucleic acid (e.g., either directly or indirectly through biotinylated nucleic acid probe) and, subsequently, the unbound and non-specifically bound population of phage are washed from the tissue slice. The binding and washing buffer can contain blocking agents including, but not limited to, casein, nonfat milk, bovine serum albumin, gelatin, tRNA, and a non-ionic detergent (e.g. Tween or NP-40).

The tissue slice having the bound phage is then contacted with a bacterial lawn so as to allow for the infection of the bacteria by the bound phage. Phage infectivity, amplification, and cell lysis is allowed to occur and the presence and position of the target nucleic acid is indicated by the appearance of a plaque on the bacterial lawn. The phage can then be isolated and used as a detection reagent on other tissue slices. By using the teachings described in this example, one can rapidly perform very sensitive in situ hybridizations. The section below describes several embodiments that are useful for the identification of the presence and location of a protein disposed on a support.

The detection of proteins disposed on a support

Methods of detecting proteins that are disposed on a support are also embodiments. As described above, a target protein can be disposed and/or separated on many types of supports including, but not limited to gels, membranes, papers, and chromatography supports. Once the target protein is disposed on the support, the target protein is contacted with a collection of phage, a phage display library, having individual phage that display a protein that interacts with a target protein. After binding and washing to remove any non-bound or non-specifically bound phage, detection is accomplished by infecting a bacterial lawn with the support-bound phage. The presence and location of plaques on the bacterial lawn will correspond to the presence and location of the target protein on the support.

Several protein/protein interactions are known and these binding proteins or fragments thereof can be expressed or attached to the surface of phage for use in identifying the presence and location of a target protein disposed on a support. Peptides that bind a target protein can include, but are not limited to, transcriptional proteins, RNA processing proteins, ligand and receptor proteins, and immunoglobins. These proteins or fragments thereof can be either expressed by phage and displayed at their surface or attached to the surface of phage using, for example, avidin/streptavidin-biotin linkages. Additionally, immunoglobulin binding domains that interact with modifications that can be incorporated into a target protein, such as biotin or dinitrophenol (DNP), can be displayed by phage. These peptides can be expressed or attached to the surface of phage so that detection of a target protein having these modifications can be accomplished.

More typically, however, phage that interact with a target protein are isolated from a phage display library. A phage display library can be created by inoculating suitable animals with the desired target protein so as to raise polyclonal antibodies to the protein, isolating total RNA from the spleens of said animals, creating cDNA from this RNA, and incorporating the cDNA into phage such that the phage display a protein encoded by the cDNA. The phage display library is then applied to a support having the target protein, non-bound and non-specifically bound phage are removed by washing, and bacterial cells are infected with the bound phage. The phage progeny that result from the infection are a highly specific reagent that can be used to detect the presence and location of the target protein, according to the methods described herein.

In another embodiment, the detection of proteins disposed on a support can be accomplished by using phage as a secondary detection reagent. Accordingly, a target protein disposed on a support is bound by an antibody that recognizes the target protein and the unbound or non-specifically bound antibody is removed. Next, a phage display library that displays a molecule that interacts with the antibody is contacted to the antibody-bound target protein. Non-bound and non-specifically bound phage are removed and the bound population of phage are allowed to infect bacterial cells present in a bacterial lawn. The appearance of a plaque on the bacterial lawn indicates the presence and location of the target protein.

Nucleic acid probes can also be attached to the surface of phage for use in identifying the presence and location of nucleic acid binding proteins disposed on a support. A nucleic acid probe can be attached to the surface of a phage through chemical modification of the proteins of the coat of the phage but, preferably, a phage expressing avidin or strepavidin or analogue thereof is attached to a biotinylated nucleic acid probe. Flexible linkers, such as λ linkers, can also be used so that the nucleic acid probe does not stericly interfere with the ability of the phage to infect a bacteria or hybridize with the target nucleic acid. Desirable lengths of linkers can be determined through routine experimentation but are of such a length to allow for attachment of the nucleic acid probe and allow for binding to the target protein and permit infection of a host bacteria.

A phage-nucleic acid reagent (i.e., the phage expressing avidin or strepavidin or an analogue thereof bound to the biotinylated nucleic acid probe) can be created and used to detect the nucleic acid binding protein. Alternatively, the biotinylated nucleic acid probe can be allowed to bind with a nucleic acid binding protein prior to contacting the nucleic acid-protein complex with a phage expressing avidin or strepavidin or an analogue thereof. Additionally, a biotinylated nucleic acid probe can be bound to the target protein prior to disposing the nucleic acid-protein complex on a support and, once on the support, the nucleic acid-protein complex can be detected by binding and amplifying phage that interact with the biotin of the nucleic acid probe. A 5' or 3' biotinylated oligonucleotide can be synthesized by conventional methods and used as the probe nucleic acid or several other methods to incorporate biotin or other modified nucleotides into nucleic acid probes are known (e.g., biotinylated RNA probes, as described supra). The following example describes an approach that can be used to detect a target protein disposed on a support.

EXAMPLE 6

Although the detection of proteins directly from a gel is made possible by using an embodiment described herein, the immobilization of the target protein on a membrane offers the advantage of stripping the blot and re-probing it with another phage display library. By one approach, the target protein is separated on a gel and immobilized to a nylon membrane, according to conventional Western or immunoblotting techniques. For example, IgG disposed on a membrane can be identified as follows.

Several serial dilutions of rabbit anti-BSA IgG (Sigma, St. Louis, Mo.) are made and the protein is separated on a SDS/PAGE gel. Subsequently, the IgG is transferred to a nylon membrane by electroblotting. The blot is rinsed three times with distilled water, and is blocked with a blocking buffer (PBS, 0.05% (v/v) Tween-20, 5% (w/v) skimmed milk, 0.5% (w/v) gelatin) at room temperature for 30 minutes, and then is rinsed three times with distilled water. A phage suspension ($10^9$ pfu/ml) is added to the blot in a binding buffer (50 mM Tris-HCl (pH 7.5), 150 mM NaCl, 0.05% Tween-20, 10 mM $MgSo_4$) at 4° C. for 12 to 16 hours. After the binding phase, the non-bound and non-specifically bound phage are removed from the blot by washing three times in binding buffer at room temperature. Subsequently, the blot is replicate plated on a bacterial lawn and is held in place for approximately 10 minutes to allow for infection of the bacteria. The bacterial plates are then incubated overnight and are then inspected for plaques. The identification of IgG and the location of the protein on the blot will be indicated by the appearance of plaques on the bacterial lawn. The teachings of this example can be applied to detect any target protein provided that the phage have a probe biomolecule that interacts specifically with a target biomolecule. The example below describes an approach that was used to determine the limits of protein detection by a method described herein.

EXAMPLE 7

To determine the limits of detection of a target protein by the system described herein, a nitrocellulose membrane (0.45 micron pore size) was spotted with a serial dilution of an anti-M13 antibody [supplied by: 5'™ 3' Prime, Inc., Boulder, Colo.] using a dot-blot manifold apparatus. The anti-M13 antibody was used to bind M13 and a bacterial lawn was subsequently infected with the antibody-bound M13. A manifold dot-blot apparatus was used for all applications including protein dilutions, application of the bacteriophage, and for applying the bacterial lawn because the manifold-clearance of phage and washing steps contained the phage better than an open-pan procedure. The 0.45 $\mu$M nitrocellulose pores were used to actively eliminate unbound phage by vacuum. Phage binding was followed by a series of pan-washes with agitation at room temperature to remove non-bound and non-specifically bound phage. The vacuum-pressure also eliminated brownian type movement of bacterial lawn in the liquid phase.

Lot #FJ 195A M13 antibody was used with a protein concentration of 8 mg/ml. Serial dilutions ranged from neat application of 10:1 stock (80 $\mu$g) in sample #1. Thus tube #2=8 $\mu$g, #3=0.8 $\mu$g, #4=80 ng, #5=8 ng, #6=0.8 ng, #7=80 pg, #8=8pg, #9=80 fg, #10=8 fg, #11=0.8 fg, #12=80 ag, #13=8 ag, #14=0.8 ag and #15=0.08 ag of protein. Dilutions were carried out serially to $10^{-30}$ in triplicates. Ten $\mu$l of each dilution was mixed with 90 $\mu$l of PBS in each well of a dot-blot manifold. Protein-containing lanes on the membrane were followed by PBS-lanes as negative controls without protein. The formulation of PBS was 150 mM NaCl with 6 mM phosphate buffer pH 7.4. On the manifold, each lane of the membrane was pre-washed with 100 $\mu$l/lane in the manifold at room temperature for 60 minutes. Following the blotting of the protein, the membrane was soaked for 10 minutes in 100 ml of a phosphate buffered saline solution containing 3% w/v Tween™ 20 (PBST).

Next, the membrane was incubated in 100 ml of a PBST solution containing $5 \times 10^{11}$ plaque forming units (pfu) of bacteriophage M13 (Ph.D.™ Peptide Display System from New England BioLabs). Following phage binding, the membrane was washed six times, for 10 minutes each wash, with 100 ml of PBST. The membrane was vacuum aspirated during the binding and washing steps to remove the bacteriophage into a closed evacuation flask containing Wescodyne solution. The membrane was removed from the manifold and the manifold was sterilized by autoclaving. Subsequently, the membrane was placed on fresh blotting paper to remove residual moisture. It was then placed on a porous support (Fast blot developer, Pierce Chemical Co., Rockford, Ill.) for 3 additional washes with 400 ml of PBST. The membrane was washed a total of nine times in three separate sterilized dishes to eliminate contamination by unbound bacteriophage.

The bacterial lawn was made from an overnight culture of E. coli in 5-ml LB broth. One ml of overnight culture was inoculated into 5 ml of LB broth+Xgal. The culture was grown at 37° C. for 1 hour (in mid-log phase) and kept on ice until use. The membrane was carefully re-inserted into the washed and autoclaved manifold for application of a suspension of 100 µl bacteria/well. The membrane was placed face up on top of a 100 mm LB agar plate with Xgal. The dish was then incubated overnight at 37° C. to allow for propagation.

The plaques that appeared on the bacterial lawn were blue because the M13 bacteriophage carried the β-galactosidase gene. This gene was lacking in the bacterial strain employed (*E.coli* strain ER2537 [(F$^-$,lacI$^q$, lacZ)M15proA$^+$B$^+$/fhuA2 supE thi (lac-proAB) (hsdMS-mcrB)5 ($r_k^-m_k^-$McrBC$^-$)]. In the experiment described above, detectable signal in triplicate repetitions was discernable to the dilution $10^{-16}$, thus, representing a reproducible limit of detection of ten molecules of protein. The theoretical level of detection was calculated as follows. Since the average protein size of the anti-M 13 antibody is 45,000 daltons, the average amino acid molecular weight is 115 daltons, and the average number of amino acid residues per protein is 391, a single protein contains $4.5 \times 10^4$ grams/mole. If Avagadro's number ($6.02 \times 10^{23}$ particles) equals the number of particlesimole, a single protein molecule would be equivalent to a weight of $7.5 \times 10^{-20}$ grams or $7.5 \times 10^{-2}$ ag. The dilution representing this limit of detection would be at $10^{-15}$.

Notably, the highest concentration of protein had almost no phage bound to the membrane. There are several explanations for this phenomenon: First, the protein present at the highest concentration would block the active binding sites. Second, any bound page might "break-off" along with pieces of protein due to the clumping during the vigorous washes to remove unbound phage. At the higher dilutions, there was no observable signal over background non-specific binding. The findings described in this example verify that a support-based embodiment can detect as little as 10 molecules of a target protein. The example below details the approach that was used to detect the presence and location of a protein separated on a gel and transferred to a membrane.

EXAMPLE 8

In this experiment, proteins (molecular weight standards [NOVEX MultiMark Multicolored Standards, supplied by: Novex, Inc., San Diego, Calif.] and antibody proteins to the phage M-13 [supplied by: 5'™ 3' Prime, Inc., Boulder, Colo.] were labeled with the fluorescent stain fluorescamine. A serial dilution of these labeled proteins were loaded on 4–12% Bis-Tris pre-cast gels [NOVEX, NuPage gels] and separated by electrophoresis. Prior to electrophoresis, the samples were heated under reducing conditions (0.5M DTT) at 70° C. for 10 minutes followed by cooling to room temperature. The molecular marker proteins were placed in well 12, and the M-13 antibody proteins were diluted in 10 fold steps and placed in wells 1 through 11. Two identical gels were prepared in this manner. Electrophoresis was conducted for 40 minutes at 200 volts in a NOVEX Xcell II mini cell containing MES.SDS running buffer (1M 2-(-N-morpholino) ethane sulfonic acid tris base, 69.3 mM SDS and 20.5 mM EDTA at pH 7.3).

Next, the separated proteins in the two gels were electroblotted onto nitrocellulose 0.45 micron pore size membranes with a blot module (NOVEX) using a transfer buffer containing 500 mM Bicine, 500 mM Bis-Tris, and 20.5 mM EDTA at pH 7.2. Following blotting, one of the membranes was made transparent with toluene and the proteins disposed on the transparent membrane were photographed using an ultraviolet transilluminator. The second blot (the membrane without toluene exposure) was soaked for 10 minutes in a phosphate buffered saline solution containing 3% w/v Tween (PBST). The membrane was then incubated in 100 ml of a PBST solution containing $5 \times 10^{11}$ plaque forming units (pfu) of bacteriophage M13 (Ph.D.™ Peptide Display System from New England BioLabs). Following this incubation the membrane was washed six times, for 10 minutes for each wash, with 100 ml of PBST. The membrane was then placed on fresh blotting paper to remove residual moisture. It was then placed on a porous support (Fast blot developer, Pierce Chemical Co., Rockford, Ill.) for 3 additional washes with 400 ml of PBST. The PBST was pulled through the membrane with a mild vacuum. Immediately following the removal of PBST, from the last wash, a suspension of bacteria (in mid-log phase) was applied to the membrane while it was still under a mild vacuum to remove the liquid associated with the bacteria. This membrane containing protein, phage and bacteria was then placed on a LB agar plate containing Xgal for overnight incubation at 37° C.

The membrane was photographed the next day. The plaques appeared blue because the M13 bacteriophage carried the β-galactosidase gene. This gene was non-functional in the bacterial strain employed (*E.coli* strain ER2537 [(F$^-$,/lacI$^q$, lacZ)M15proA$^+$B$^+$/fhuA2 supE thi (lac-proAB) (hsdMS-mcrB)5 ($r_k^-m_k^-$McrBC$^-$)].

Three fluorescent Protein bands I, II and III were seen in the lanes loaded with M-13 antibody proteins (lanes 1–11). Band III represented the IgG light chain, band II represented the IgG heavy chain and band I represented the heavy-light chain complex. In this denatured electrophoresis system the phage detection appeared to be most effective for the IgG heavy chain and heavy-light chain complex. Given that the limit of detection of fluorescamine labeled proteins was at about the 1 ng level, as observed in lane 3 of the gel and lane 2 after blotting on the membrane, and since dilutions for each lane were 10 fold, the proteins detected in lane 11 represented approximately 1–10 atto-moles. Given an approximate molecular weight of 30 kD for the heavy chain this amount corresponds to a detection of as little as 100 molecules. The findings described in this example verify that as little as 100 molecules of a protein can be detected by a gel-based embodiment. In the example that follows, a method for in situ protein localization is provided.

EXAMPLE 9

A highly sensitive method of in situ protein localization is another embodiment. By this approach, a tissue is sectioned and preserved according to conventional techniques, and, subsequently, bound with a phage library having phage that display a molecule that binds to a target protein in the tissue slice. The phage library is contacted with the tissue slice for a period long enough to allow for the phage to bind to the desired target protein and then the unbound and non-specifically bound population of phage are washed from the tissue slice. Next, the tissue slice having the bound phage is contacted with a bacterial lawn so as to allow for the infection of the bacteria by the bound phage. Phage infectivity, amplification, and cell lysis is allowed to occur and the presence and position of the target protein is indicated by the appearance of a plaque on the bacterial lawn. The phage can then be isolated and used as a detection reagent on other tissue slices. By using the teachings described in this example, one can rapidly perform very sensitive in situ protein localization. The next section describes several diagnostic embodiments.

Diagnostic applications

Methods for determining whether a target biomolecule is present in an biological sample are also embodiments. Accordingly, a biological sample is obtained from a subject in need of a diagnostic test. The sample can have a target molecule that is a nucleic acid, protein, or both. The biological sample is then disposed on a support. Preferably, the target molecule is prepared for analysis (e.g., isolation of the nucleic acid or protein depending on the nature of the assay) prior to disposing the sample onto a support, however, it is not necessary to perform such a step to practice this embodiment. Next, a collection of phage displaying a binding molecule that interacts with the target biomolecule is brought into contact with the immobilized sample. Many types of supports are suitable for use with this embodiment. Membranes, gels, affinity support resins, dipsticks, and other macromolecular structures can be used, for example, to adhere to the biological sample. The unbound and nonspecifically bound phage are washed from the support and the bound phage are replicated in a suitable host. The diagnosis of the presence of the target biomolecule is then determined by the appearance of cell lysis of the bacterial host.

Diagnostic kits having phage that display a binding molecule that interacts with a protein or nucleic acid associated with a disease state are also embodiments. These diagnostic kits can have a support, bacteria, culture media, positive and negative control-sample biomolecules, and instructions. The following section describes the manufacture of active ingredients for pharmaceuticals based on the technology described herein.

Therapeutic applications

Methods for generating a novel class of components for pharmaceutical agents are also embodiments. By one approach, a support having disposed thereon a target biomolecule is brought into contact with a randomly generated phage display library. Individual phage in the phage display library display a binding molecule that recognizes target biomolecule disposed on the support. The non-bound and non-specifically bound population of phage are then removed from the support. The bound population of phage are replicated in a host bacteria and the phage are isolated from the replicated population of phage. Subsequently, the isolated phage are incorporated into a pharmaceutical product. Alternatively, the nucleic acid encoding the binding protein is sequenced and the sequence of the binding peptide is determined. From this sequence, synthetic peptides are generated and these molecules are formulated into pharamaceuticals. Further, approaches in rational drug design can be performed on the sequences identified as binding to the target protein so as to generate more molecules (e.g., peptidomimetics and chemicals) for incorporation into pharmaceuticals.

By using the approaches described above, therapeutic agents specific for a patient's particular disease can be generated. In one embodiment, for example, a virus from an infected patient is obtained and the proteins of the virus are disposed on a support. The procedure detailed above is performed and phage that bind to the viral protein are identified as a vaccine component and are incorporated into a pharmaceutical product.

In order to generate a phage display library having a phage that displays a protein that interacts with a target viral protein an additional procedure can be employed. By way of example and not by limitation, a phage display library can be created by first injecting the virus or viral protein into a host animal to generate an immune response. The host animal is then sacrificed and the nucleic acid from its spleenocytes is obtained. Nucleic acid corresponding to immunoglobulin sequences is amplified by PCR and is cloned into phage by conventional techniques. In this manner, binding proteins specific for the viral protein can be expressed on the surface of the phage. (See e.g., Merz et al., *J. Neurosci. Methods* 62:213 (1995)).

Methods for making a therapeutic kit are also embodiments. One embodiment of the therapeutic kit, for example, has a support that is used to dispose a biomolecule such as a protein or a nucleic acid. The therapeutic kit further comprises a collection of phage wherein individual phage in the collection display a molecule that interacts with a desired protein that is disposed on the solid matrix. Additionally, the therapeutic kit can have a host bacteria that can be infected by the phage after it has bound to the desired protein and instructions.

The therapeutic kit is used by disposing the target biomolecule on the support, contacting the target biomolecule with the phage displaying a molecule that interacts with the target biomolecule, washing the unbound or non-specifically bound phage from the support, and replicating the bound phage in the host bacteria. The replicated phage are then isolated from the bacteria and are incorporated into a therapeutic agent, a prophylactic agent, or a pharmaceutical The pharmacologically active compounds described herein can be processed in accordance with conventional methods of galenic pharmacy to produce medicinal agents for administration to patients, e.g., mammals including humans. The phage isolated according to the embodiments described above can be incorporated into a pharmaceutical product with and/or without modification. Further, pharmaceuticals or therapeutic agents that deliver the phage or a nucleic acid sequence encoding the phage by several routes can be manufactured. For example, and not by way of limitation, the use of DNA, RNA, and viral vectors having sequence encoding the phage is contemplated. Nucleic acids encoding a desired phage can be administered alone or in combination with the phage.

The phage or nucleic acids encoding them can be employed in admixture with conventional excipients, i.e., pharmaceutically acceptable organic or inorganic carrier substances suitable for parenteral, enteral (e.g., oral) or topical application that do not deleteriously react with the active compounds. Suitable pharmaceutically acceptable carriers include but are not limited to water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilizates obtained, for example, for the preparation of products for injection.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of detecting electrophoretically separated biomolecules comprising the steps of;
   (a) obtaining a solid matrix having disposed thereon a plurality of electrophoretically separated biomolecules;
   (b) contacting the solid matrix with a collection of phage, wherein individual phage in the collection have a phage-expressed binding protein so that the collection of phage in aggregate comprises a collection of phage-expressed binding proteins, and wherein contact of the solid matrix and the collection of phage results in a non-bound population of phage and a bound population of phage;
   (c) removing the non-bound population of phage to leave the bound population of phage localized to positions on the solid matrix corresponding to positions of the electrophoretically separated biomolecules;
   (d) replicate plating by placing the bound population of phage in contact with a bacterial lawn having host bacteria for the phage under conditions that permit the bound phage to infect the host bacteria so as to produce a replicated population of phage; and
   (e) detecting the replicated population of phage, whereby electrophoretically separated biomolecules are detected.

2. The method of claim 1, wherein the phage-expressed binding protein has joined thereto a linked or un-linked protein or nucleic acid that can bind to a target biomolecule, wherein the linked or unlinked protein or nucleic acid is bound to the target biomolecule to provide a bound phage.

3. The method of claim 1 further comprising the step of isolating at least one phage from the replicated population of phage.

4. The method of claim 3 further comprising the step of incorporating the phage into a pharmaceutical product.

5. The method of claim 3, further comprising the step of incorporating the phage into a diagnostic kit.

* * * * *